US011052177B2

(12) United States Patent
Lee et al.

(10) Patent No.: US 11,052,177 B2
(45) Date of Patent: Jul. 6, 2021

(54) ANTIMICROBIAL POLYMER LAYERS

(71) Applicant: THE TRUSTEES OF THE UNIVERSITY OF PENNSYLVANIA, Philadelphia, PA (US)

(72) Inventors: Hyun-Su Lee, Wayne, PA (US); David M. Eckmann, Wynnewood, PA (US); Russell Composto, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 14/479,536

(22) Filed: Sep. 8, 2014

(65) Prior Publication Data

US 2015/0071982 A1 Mar. 12, 2015

Related U.S. Application Data

(60) Provisional application No. 61/874,744, filed on Sep. 6, 2013.

(51) Int. Cl.
| | |
|---|---|
| *A61L 29/08* | (2006.01) |
| *A61L 29/16* | (2006.01) |
| *A61L 31/10* | (2006.01) |
| *A61L 15/22* | (2006.01) |
| *A61L 27/34* | (2006.01) |
| *A61L 31/16* | (2006.01) |

(Continued)

(52) U.S. Cl.
CPC ........... *A61L 29/085* (2013.01); *A61L 15/225* (2013.01); *A61L 15/46* (2013.01); *A61L 27/34* (2013.01); *A61L 27/54* (2013.01); *A61L 29/16* (2013.01); *A61L 31/10* (2013.01); *A61L 31/16* (2013.01); *A61L 2300/404* (2013.01); *A61L 2300/406* (2013.01); *A61L 2420/02* (2013.01); *A61L 2420/08* (2013.01)

(58) Field of Classification Search
None
See application file for complete search history.

(56) References Cited

U.S. PATENT DOCUMENTS

| | | | |
|---|---|---|---|
| 4,918,016 | A | 4/1990 | Leuba et al. |
| 5,208,166 | A | 5/1993 | Saunders et al. |

(Continued)

FOREIGN PATENT DOCUMENTS

WO  WO 2012/109239  8/2012

OTHER PUBLICATIONS

Liermann et al., Microenvironments of pH in biofilms grown on dissolving silicate surfaces, Chemical Geology (2000), vol. 171, pp. 1-16.*

(Continued)

*Primary Examiner* — Aradhana Sasan
(74) *Attorney, Agent, or Firm* — Mark S. Cohen; Pearl Cohen Zedek Latzer Baratz LLP

(57) ABSTRACT

The invention provides compositions comprising a plurality of polymer layers for preventing or inhibiting microbial infections. Specifically, the invention provides a combination of a cationic polymer layer that resists adhesion of a microbe to its surface and an anionic polymer layer that releases a cationic anti-microbial agent in response to a change in pH or electrostatic balance.

30 Claims, 16 Drawing Sheets

(51) Int. Cl.
*A61L 15/46* (2006.01)
*A61L 27/54* (2006.01)

(56) References Cited

U.S. PATENT DOCUMENTS

| | | | |
|---|---|---|---|
| 5,698,190 A * | 12/1997 | Hider | C08F 8/30 |
| | | | 424/78.08 |
| 5,830,883 A | 11/1998 | Block et al. | |
| 5,900,408 A | 5/1999 | Block et al. | |
| 6,852,353 B2 * | 2/2005 | Qiu | A61L 27/34 |
| | | | 427/164 |
| 2002/0102208 A1 | 8/2002 | Chinn et al. | |
| 2003/0134120 A1 | 7/2003 | Kim et al. | |
| 2003/0219533 A1 | 11/2003 | Chabrecek et al. | |
| 2003/0232088 A1 | 12/2003 | Huang et al. | |
| 2006/0134158 A1 | 6/2006 | Majima et al. | |
| 2006/0177489 A1 | 8/2006 | Massouda et al. | |
| 2007/0085059 A1 | 4/2007 | Mora-Gutierrez et al. | |
| 2008/0102122 A1 * | 5/2008 | Mahadevan | A01N 59/16 |
| | | | 424/484 |
| 2009/0032027 A1 | 2/2009 | McCachren et al. | |
| 2009/0239084 A1 | 9/2009 | Bristow et al. | |
| 2009/0275906 A1 * | 11/2009 | Berland | A61L 15/225 |
| | | | 604/359 |
| 2009/0293893 A1 | 12/2009 | Mishra et al. | |
| 2010/0003212 A1 | 1/2010 | Kis et al. | |
| 2010/0015447 A1 | 1/2010 | Lahann et al. | |
| 2010/0233434 A1 | 9/2010 | Lahav et al. | |
| 2010/0280452 A1 * | 11/2010 | Chen | A61L 29/085 |
| | | | 604/103.01 |
| 2010/0291306 A1 | 11/2010 | Tsuchida et al. | |
| 2013/0210692 A1 | 8/2013 | Gutowski et al. | |

OTHER PUBLICATIONS

Park et al., pH-Sensitive Bipolar Ion-Permselective Ultrathin Films, J. Am. Chem. Soc. (2004), vol. 126, p. 13723-13731.*
Aranaz et al., Current Organic Chemistry, vol. 14, pp. 308-330. (Year: 2010).*
Lee et al., "The effect of non-specific interactions on cellular adhesion using model surfaces", Biomaterials 26, 2005, 1721-1730.

* cited by examiner

ANTIMICROBIAL POLYMER LAYERS

CROSS-REFERENCE TO RELATED APPLICATIONS

This application claims priority to and the benefit of U.S. Provisional Patent Application 61/874,744, filed Sep. 6, 2013, which is incorporated by reference herein in its entirety.

STATEMENT OF GOVERNMENT INTEREST

This invention was made with government support under grant number R01 HL060230 awarded by the National Institutes of Health. The United States government has certain rights in the invention.

FIELD OF THE INVENTION

The invention relates generally to compositions comprising a plurality of polymer layers for preventing or inhibiting microbial infection. Specifically, the invention relates to a combination of a cationic polymer layer that resists adhesion of a microbe to its surface and an anionic polymer layer that releases a cationic anti-microbial agent in response to a change in pH or electrostatic balance.

BACKGROUND OF THE INVENTION

Hospital acquired infections are the fourth leading cause of death in the United States. About 10% of patients are infected at an annual additional medical cost of $5 billion. Most, if not all, devices including heart valves, catheters, and orthopedic implants eventually become infected with microbes. Worldwide, biomedical devices and tissue engineering are a $180 billion per year industry, but not much progress has been made to prevent these infections.

The microbes can come from the skin flora, poor aseptic techniques or contamination of the device itself. Major bacterial offenders include coagulase-negative *staphylococcus, S. aureus* and gram-negative *bacilli* (e.g., *P. aeruginosa*). Despite the introduction of best practices (e.g., hand washing) at hospitals, bloodstream infections remain a major problem. Moreover, Medicare and Medicaid will no longer reimburse facilities for the costs associated with these infections.

Antibacterial surfaces using synthetic polymers with quaternary ammonium salts, covalently grafted antibiotic surface, and silver impregnated polymer surfaces are known. Poly(methacrylic acid) (PMAA) hydrogels using polyelectrolyte multilayers and crosslinking methods for reversible loading of multi-cationic molecules are also known. Recently, polyelectrolyte multilayers (PEMs) have been investigated because PEMs can exhibit bacterial adhesion resistance, contact killing, and biocide leaching strategies. However, these polymer layers lack efficacy.

Generally, medical devices lack antibacterial coatings at present. Accordingly, there exists a need for improved antibacterial coatings.

SUMMARY OF THE INVENTION

The present inventors have developed a simple, efficient approach to generate multifunctional grafted polymer bilayers on biomaterials by chemically combining "a biopolymer" as an outer layer and "a synthetic polymer" as an inner layer. pH-responsive, biocompatible properties have been imparted to the outer layer, which, in a clinical application is typically in direct contact with a biological system. pH-responsive, drug-tunable uptake and release properties have been designed into the inner layer, which, in a clinical application, is typically in direct contact with the biomaterial and not in direct contact with the biological system. As a result, the loaded drug (e.g., an antibiotic) in the inner layer does not become exposed to the biological system until it is needed, which in the case of an antibiotic has the advantage, among others, that the development of antibiotic resistance may be reduced.

In one aspect, provided herein are anti-microbial materials, the anti-microbial materials include: a plurality of polymer layers and an anti-microbial agent (e.g., an antibiotic such as an aminoglycoside) sequestered therein, the plurality of polymer layers comprise a first polymer comprising an anionic polymer (e.g., poly(acrylic acid) (PAA), alginic acid (ALG), poly(aspartic acid), poly(glutamic acid) (PGA), hyaluronic acid, or poly(styrenesulfonate)) and a second polymer layer comprising a cationic polymer (e.g., chitosan, chitosan modified with a quaternary ammonium salt or carboxylic acid) overlaying said first polymer layer, wherein said first polymer layer is immobilized on the surface of said substrate, and wherein said second polymer layer overlays said first polymer layer, wherein said agent remains sequestered at a physiological pH, and wherein said polymers are configured to release said agent at an acidic pH.

In another aspect, provided herein are articles, the articles include: a substrate comprising a surface, a first polymer layer comprising an anionic polymer, and a second polymer layer comprising a cationic polymer, wherein said first polymer layer is immobilized on the surface of said substrate, and wherein said second polymer layer overlays said first polymer layer. In some embodiments, the article further has an agent (e.g., an antibiotic such as an aminoglycoside) sequestered in said first polymer layer, and where in some cases the agent is sequestered at a physiological pH, and is released at a second pH, such as an acidic pH. In some embodiments, the substrate is a medical material, device, or implant.

In another aspect, methods for providing an anti-microbial coating on a surface of an article are disclosed, the methods include the steps of: immobilizing an anionic polymer on the surface of said article to form a first polymer layer; coating a cationic polymer on the first polymer layer to form a second polymer layer; and sequestering an anti-microbial agent in said anionic polymer. In some embodiments, the step of sequestering the anti-microbial agent comprises the steps of loading the first polymer layer with the anti-microbial agent by exposing the first polymer layer to an acidic pH in the presence of the anti-microbial agent; and raising the pH to a physiological pH. In some embodiments, the methods further comprise the step of drying the anti-microbial coating on the surface of the article.

In another aspect, methods for preventing or inhibiting a microbial infection associated with the use of a medical material, device, or implant are provided, the methods include: providing a medical material, device, or implant having a surface coated with an anti-microbial material described herein; and contacting the coated medical material, device, or implant with a potential source of the microbial infection.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
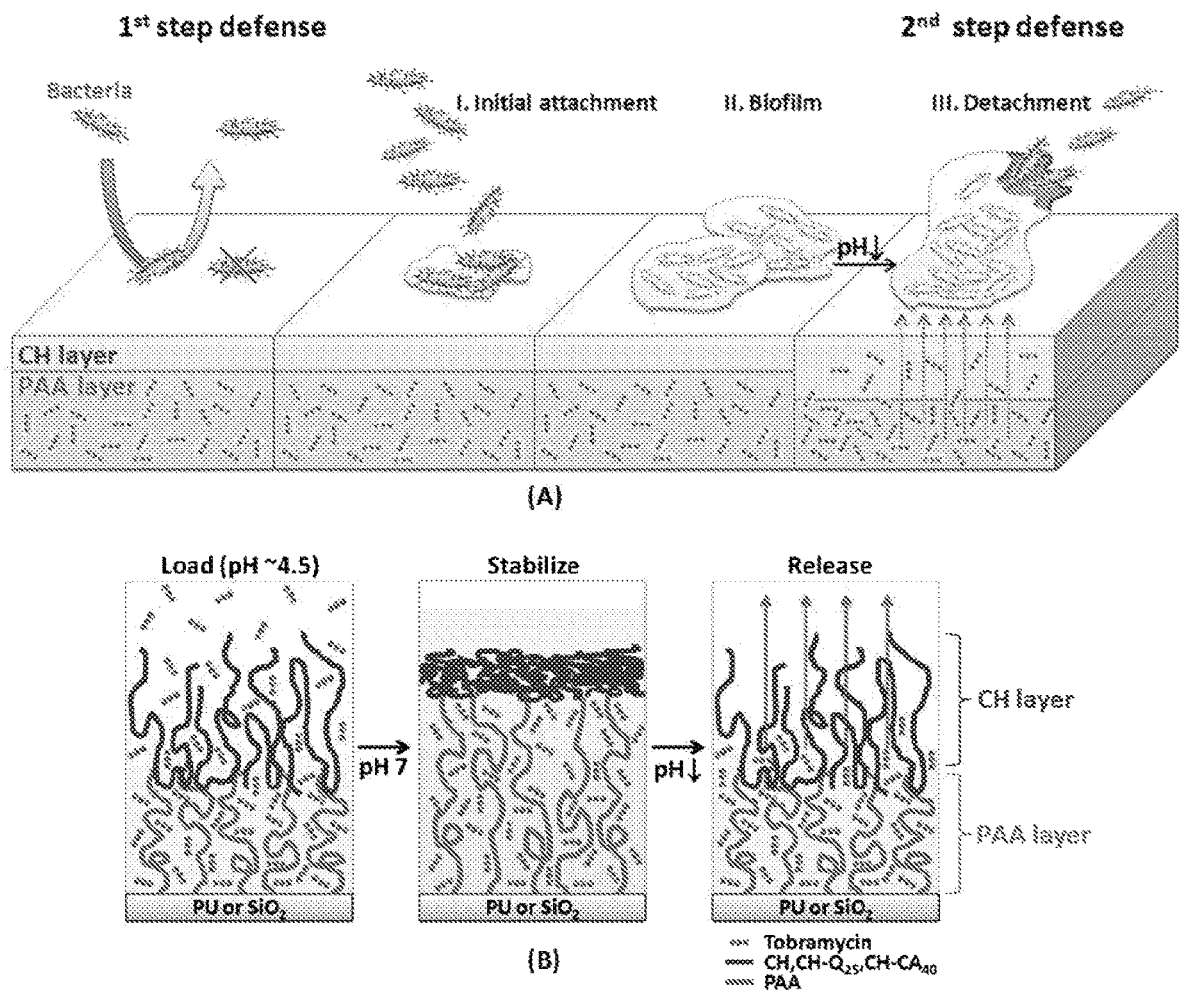
FIG. 1. (A) A polymer bilayer system with a novel two-step defense strategy; during an initial stage (I) of bacterial attachment, the outer layer repels or kills bacteria to prevent their adhesion on the surface. During the second stage, if bacterial colonization and biofilm formation on the surface (II) does occur, the inner layer releases antimicrobial agents to kill bacteria (III). The release is triggered by a local decrease in pH near the infected area due to the bacterial colonization and biofilm formation. (B) The outer (light grey) and inner (dark grey) layers can be a cationic polymer (e.g., chitosan or related copolymer) and an anionic polymer (e.g., poly(acrylic acid); "PAA"), respectively. An antibiotic (e.g., tobramycin; "TOB," open circles) is loaded in the anionic polymer (e.g., PAA) at pH~4.5, stored at pH 7 and released at low pH. At pH 7, the cationic polymer (e.g., CH, CH-Q25, or CH-CA40) inhibits bacteria attachment and shields antibiotic until infection begins.

The invention provides compositions and methods for preventing or inhibiting microbial infections. Specifically, the invention provides compositions that comprise a plurality of polymer layers, for example, a cationic polymer layer that resists adhesion of a microbe to its surface and an anionic polymer layer that releases a cationic anti-microbial agent in response to a change in electrostatic balance.

In one aspect, provided herein are anti-microbial materials, the anti-microbial materials include: a plurality of polymer layers and an anti-microbial agent (e.g., an antibiotic such as an aminoglycoside) sequestered therein, the plurality of polymer layers comprise a first polymer comprising an anionic polymer (e.g., poly(acrylic acid) (PAA), alginic acid (ALG), poly(aspartic acid), poly(glutamic acid) (PGA), hyaluronic acid, or poly(styrenesulfonate)) and a second polymer layer comprising a cationic polymer (e.g., chitosan, chitosan modified with a quaternary ammonium salt or carboxylic acid) overlaying said first polymer layer, wherein said first polymer layer is immobilized on the surface of said substrate, and wherein said second polymer layer overlays said first polymer layer, wherein said agent remains sequestered at a physiological pH, and wherein said polymers are configured to release said agent at an acidic pH.

In another aspect, provided herein are articles, the articles include: a substrate comprising a surface, a first polymer layer comprising an anionic polymer, and a second polymer layer comprising a cationic polymer, wherein said first polymer layer is immobilized on the surface of said substrate, and wherein said second polymer layer overlays said first polymer layer. In some embodiments, the article further has an agent (e.g., an antibiotic such as an aminoglycoside) sequestered in said first polymer layer, and where in some cases the agent is sequestered at a physiological pH, and is released at a second pH, such as an acidic pH. In some embodiments, the substrate is a medical material, device, or implant.

In another aspect, methods for providing an anti-microbial coating on a surface of an article are disclosed, the methods include the steps of: immobilizing an anionic polymer on the surface of said article to form a first polymer layer; coating a cationic polymer on the first polymer layer to form a second polymer layer; and sequestering an anti-microbial agent in said anionic polymer. In some embodiments, the step of sequestering the anti-microbial agent comprises the steps of loading the first polymer layer with the anti-microbial agent by exposing the first polymer layer to an acidic pH in the presence of the anti-microbial agent; and raising the pH to a physiological pH. In some embodiments, the methods further comprise the step of drying the anti-microbial coating on the surface of the article.

In another aspect, methods for preventing or inhibiting a microbial infection associated with the use of a medical material, device, or implant are provided, the methods include: providing a medical material, device, or implant having a surface coated with an anti-microbial material described herein; and contacting the coated medical material, device, or implant with a potential source of the microbial infection.

Applicants surprisingly and unexpectedly found that microbial infections associated with a medical material, device, or implant can be effectively inhibited by providing a coating that comprises a cationic polymer layer (e.g., chitosan) that resists adhesion of a microbe to its surface and an anionic polymer (e.g., poly(acrylic acid)) layer that releases a cationic anti-microbial agent (e.g., tobramycin) in response to a change in electrostatic balance.

The cationic polymer layer comprises positively charged cations, and thus capable of resisting adhesion of a cationic microbe. The cationic polymer layer is a pH responsive cationic polymer. At a physiological pH, the cationic polymer can form a dense layer, which is capable of preventing the release of an agent in the anionic polymer layer and also capable of shielding the agent from outer environment. At an acidic pH, the cationic polymer can swell and thereby allow the release of an agent in the anionic polymer layer.

The cationic polymer layer may include one or more of a suitable cationic polymer known in the art. Preferably, the cationic polymer layer includes chitosan. Chitosan is a polymer well known in the art and described in U.S. Pat. Nos. 5,900,408; 5,830,883; 5,208,166; and 4,918,016 and United States Patent Application Publications 20030134120; 20060134158; 20060177489; 20090239084; and 20100291306, all of which are incorporated by reference herein in their entirety.

Chitosan is a linear polysaccharide composed of randomly distributed β-(1-4)-linked D-glucosamine (deacetylated unit) and N-acetyl-D-glucosamine (acetylated unit). Chitosan can be produced by any method known in the art. For example, chitosan may be produced by the deacetylation of chitin, which is the structural element in the exoskeleton of crustaceans (e.g., crabs, shrimp) and cell walls of fungi. Chitin may be treated with strong alkalis to remove acetyl groups producing chitosan. Depending on the specific treatment of chitin, chitosan may vary in the degree of deacetylation.

In particular embodiments, chitosan is modified with a quaternary ammonium salt. Quaternary ammonium salts are salts of quaternary ammonium cations with an anion. Quaternary ammonium cations, also known as quats, are positively charged polyatomic ions of the structure $NR_4^+$, R being an alkyl group or an aryl group.

In some embodiments, the chitosan is modified with carboxylic acid. Chitosan can be modified with a quaternary ammonium, carboxylic acid, or its combinations by any method known in the art.

The modified chitosan may be operably linked to one or more other molecules, including but not limited to an antimicrobial molecule (e.g., antimicrobial peptide), an adhesion resistant molecule (e.g., polyethylene glycol), a biocide leaching molecule, or a combination thereof. The term "operably linked," in this context, refers to chitosan and the other molecules being arranged so that they function in concert for their intended purposes. For example, the modified chitosan is operably linked to one or more other molecules by chemical conjugation. Other suitable linking methods known in the art may also be used.

Other suitable cationic polymers can also be used. In some embodiments, the cationic polymer includes, but is not limited to, poly(allylamine hydrochloride) or polyallylguanidinium. In other embodiments, the cationic polymer includes a copolymer composed of (meth)acrylic acid di C1-C2 alkyl amino C2-C4 alkyl and a monomer unit selected from (meth)acrylic acids C1-C4 alkyl, (meth) acrylic acids monohydroxy C2-C4 alkyl or a combination thereof, more preferably methyl(meth)acrylate.butyl(meth)

acrylate.(meth)acrylic acid dimethylaminoethyl copolymer; preferably methyl methacrylate.butyl methacrylate.methacrylic acid dimethylaminoethyl copolymer. Methyl methacrylate.butyl methacrylate.methacrylic acid dimethylaminoethyl copolymer is commercially available as EUDRAGIT E-100® (Degussa Corporation, Germany, Dusseldorf).

The anionic polymer layer comprises negatively charged anions, and thus may attract a cation through an electrostatic attraction. Preferably, at a physiological pH, the cationic agent is electrostatically linked to the anionic polymer. At an acidic pH, the charge on anionic polymer layer is reduced, and as a result, the agent is no longer attracted to the anionic polymer layer, and is released from the anionic polymer layer.

The term "physiological pH," as used herein refers to a pH ranging from about 7.0 to about 7.5, and preferably, ranging from about 7.35 to about 7.45.

The term "acidic pH," as used herein refers to a pH ranging from about 2.0 to about 6.9. For example, an acidic pH may be caused by or associated with a bacterial infection of a biofilm.

The anionic polymer layer may include one or more anionic polymers known in the art. In some embodiments, the anionic polymer layer includes poly(acrylic acid) (PAA). PAA is a polymer well known in the art and described in United States Patent Application Publications 20130210692; 20100233434; 20100015447; 20090293893; and 20030232088, all of which are incorporated by reference herein in their entirety.

Poly(acrylic acid) (PAA or Carbomer) is a generic name for synthetic high molecular weight polymers of acrylic acid. They may be homopolymers of acrylic acid, crosslinked with an allyl ether pentaerythritol, allyl ether of sucrose or allyl ether of propylene.

Other suitable anionic polymers can also be used. Examples of an anionic polymer include, but is not limited to, alginic acid (ALG), poly(aspartic acid), poly(glutamic acid) (PGA), hyaluronic acid, poly(styrenesulfonate), cellulose acetate phthalate, hydroxypropyl methylcellulose.phthalate, hydroxypropyl methylcellulose.acetate.succinate or (meth)acrylic acid.methyl(meth)acrylate copolymer, more preferably (meth)acrylic acid.methyl(meth)acrylate copolymer, more preferably methacrylic acid.methyl(meth)acrylate copolymer. This methacrylic acid.methyl(meth)acrylate copolymer is, for example, commercially available as EUDRAGIT S-100® (Degussa Corporation, Germany, Dusseldorf).

The cationic and anionic layers in the bilayer system can exhibit opposite pH dependent swelling behavior. The swelling properties of the bilayer systems can be tuned, for example, by varying the thickness of layers, molecular weight of polymers, modifications of polymers, and the pH of the solution.

In some embodiments, the molecular weight of a polymer may range from about 1 to about 500 kDa. In other embodiments, the molecular weight of a polymer may range from about 2.0 to about 250 kDa. In other embodiments, the molecular weight of a polymer may range from about 3.0 kDa to about 75 kDa. In other embodiments, the molecular weight of a polymer may range from about 3.5 kDa to about 50 kDa. In other embodiments, the molecular weight of a polymer is 500, 300, 200, 150, 100, 50, 10, 5, 4, 3.5, 3, 2, or 1 kDa.

In some embodiments, polymers may be in the form of a nanoparticle. As used herein, a "nanoparticle" is a particle having a diameter of from approximately 1 to approximately 500 nanometer (nm), having any size, shape or morphology, known in the art. In one embodiment, the diameter of each nanoparticle ranges between 1 nm and 500 nm. In another embodiment, the diameter of each nanoparticle ranges between 50 nm and 300 nm. In another embodiment, the diameter of each nanoparticle ranges between 100 nm and 200 nm. In one embodiment, the diameter of each nanoparticle is about 500, 300, 200, 150, 100, 50, or 5 nm.

The antimicrobial agent may include a cation. In some embodiments, the agent may include an amine group. Any suitable agent capable of inhibiting the growth of or killing microorganisms can be used. Other agents can also be used. In some embodiments, a combination of anti-microbial agents and other agents can be used.

Examples of agents include, for example, but not limited to, antibiotics, antiseptics, antiviral agents, enzyme inhibitors, antipyretics, and local anesthetics.

Antibiotics are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, tobramycin, erythromycin, quinolones (including but not limited to ciprofloxacin), cephalosporins, geldanamycin and analogs thereof. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone. In some embodiments, the agent is anti-bacterial agent capable of inhibiting or killing bacteria, for example, but not limited to *Staphylococcus aureus* and *Pseudomonas aeruginosa*. In some embodiments, the anti-bacterial agent is an aminoglycoside.

Antiseptics are substances that prevent or arrest the growth or action of microorganisms. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Antiviral agents are substances capable of destroying or suppressing the replication of viruses. Examples of antiviral agents include methyl-p-adamantane methylamine, hydroxy ethoxymethylguanine, adamantanamine, 5-iodo-2'-deoxyuridine, trifluoro thymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine, 1-hydroxymaleate, iodotubercidin, p-bromotetramisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl, L(-), deprenyl HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacin, 2-cyclooctyl-2-hydroxyethylamine hydrochloride, 2,3-dichloro-alpha-methylbenzylamine, 8,9-dichloro-2,3,4,5-tetrahydro~IH-2-benzazepine hydrochloride, p-aminoglutethimide, p-aminoglutethimide tartrate, R(+), p-aminoglutethimide tartrate, S(-), 3-iodo tyrosine, alpha-methyltyrosine, L(−), alpha-methyltyrosine, D L(−), cetazolamide, dichlorphenamide, 6-hydroxy-2-benzothiazolesulfonamide, and allopurinol.

Antipyretics are substances capable of relieving or reducing fever. Anti-inflammatory agents are substances capable of counteracting or suppressing inflammation. Examples of such agents include aspirin (acetylsalicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which inhibit pain signals in a localized region. Examples of such anesthetics include procaine, lidocaine, bupivicaine and ropivicaine.

In some embodiments, provided herein are methods of making an article comprising a plurality of polymer layers, the method comprising: preparing an anionic polymer layer; loading an agent to said anionic polymer layer; grafting or immobilizing said anionic polymer layer to a surface; reacting with a cationic polymer to form a cationic polymer layer. In yet other embodiments, provided herein is are methods for coating antimicrobial polymer layers on an article, the method comprising: providing a cationic and an anionic polymer layers; loading said anionic polymer layer with an antimicrobial agent; grafting or immobilizing said loaded anionic polymer layer to a surface of said article; grafting or immobilizing said cationic polymer layer to said loaded anionic polymer layer, which is grafted or immobilized to said surface.

The inner anionic polymer can be immobilized or otherwise grafted on any suitable surface. In one embodiment, the surface is a hard surface (e.g., metal, glass). In another embodiment, the surface is a soft surface (e.g., polymer). The immobilization or grafting methods may be chosen based on surface type or other factors, known to one skilled in the art.

Articles of the present invention have at least two layers of polymers (e.g., an anionic layer and a cationic layer) thereon. In some embodiments, articles of the present invention have a plurality of anionic layers and a plurality of cationic layers.

The layers may be provided as a coating or as a preformed film which is secured to at least a portion of an article and generally to an exterior surface thereof. The layers are preferably self-adhering layers.

The layer may be of any desired thickness to serve its purpose. In one embodiment, the coating thickness ranges from about 5 nm to about 100 nm. In another embodiment, the coating thickness ranges from about 10 nm to about 80 nm. In another embodiment, the coating thickness ranges from about 30 nm to about 70 nm. In another embodiment, the coating thickness ranges from about 40 nm to about 60 nm. In one embodiment, the coating thickness is 100, 90, 80, 70, 60, 50, 40, 30, 20, 10, or 5 nm.

Articles comprising the coated surface of the present invention may be in the form of or comprise a film, membrane, laminate, fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, spinning, spun bonding, melt blowing, spun lacing, or carding.

The articles of the present invention provide multiple uses, because many articles benefit from a reduction in microbial growth and a wide variety of polymers are included in the present invention.

Examples of applications include, but are not limited to, antibacterial, biosensor, nano-fluidic, and drug delivery applications.

Articles of the present invention can be used in wide variety of products, for example, but not limited to, medical materials, devices, or implants, such as catheters (e.g., to prevent catheter related blood stream infection), bandages, adhesives, gauze strips, gauze pads, medical or surgical drapes, syringe holders, sutures, IV tubing, IV bags, stents, guide wires, prostheses, orthopedic pins, dental materials, pacemakers, heart valves, artificial hearts, knee and hip joint implants, bone cements, vascular grafts, urinary catheter, ostomy ports, orthopedic fixtures, pacemaker leads, defibrillator leads, ear canal shunts, cosmetic implants, ENT (ear, nose, throat) implants, staples, implantable pumps, hernia patches, plates, screws, blood bags, external blood pumps, fluid administration systems, ventilators, endotracheal tubes, heart-lung machines, dialysis equipment, artificial skin, ventricular assist devices, hearing aids, and dental implants.

Medical equipment that comes into contact with the environment (e.g., ventilators, endotracheal tubes) can be coated with polymer layers of the invention to provide antibacterial capability, such as MRSA resistance and for infection acquisition and transmission control. Polymer layers can also be applied to implantable medical devices because it is biocompatible. Cell binding motifs can be attached to polymer layer coatings so that tissue ingrowth can take place in conjunction with bacterial resistance.

The current invention is also useful in reducing or preventing biofilm growth on the surface of biomedical separation membranes, for example, but not limited to, pervaporation, dialysis, reverse osmosis, ultrafiltration, and microfiltration membranes.

Devices used in fluid, e.g., water, transportation and/or storage can also benefit from the antimicrobial material of the invention. Exemplary devices include, but are not limited to, pipes and tubes.

In order to impart antimicrobial functionality to the articles described herein, the article can be treated with the polymer layers of the invention before it is manufactured, or after, or at any time during its manufacture. For example, in making an antimicrobial medical ventilator tube, material having a surface that comprises an effective amount of polymers can be treated according to methods described herein, followed by fashioning a medical ventilator tube from the treated material. Alternatively, the polymer treatment may be performed after the material is made into a medical ventilator tube.

The term "antibacterial," as used herein, refers to bactericidal as is commonly known in the art. The number of bacteria present after contact with an antibacterial material is substantially reduced from the number initially present. The number of bacteria present may be measured as colony forming units.

The term "antimicrobial," as used herein, refers to antibacterial as well as having fungicidal and antiviral activities as is commonly known in the art.

The term "surface" may refer to the outer or topmost boundary of a material. Types of surfaces include properties such as being flat and solid such as of a film, fibrous as in fabric, porous as in a filter, rough, or permeable.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Any reference including patents, patent applications, or scientific publications, cited herein, are incorporated by reference in their entirety.

The following examples are presented in order to more fully illustrate the preferred embodiments of the invention. They should in no way be construed, however, as limiting the broad scope of the invention.

EXAMPLES

Example 1

A Two Stage Mechanism for Preventing Bacterial Infection Using a Nano-Engineered Grafted Polymer Bilayer A novel two-stage surface coating system was designed to prevent the initial adhesion of bacteria onto biomaterial and other surfaces, as well as to release microbicidal agents sequestered within the surface coating to eradicate infection should the later stage formation of biofilm occur. The bilayer system contains complementary outer and inner polymer brush layers that interfere with the ability of bacteria to adhere and, if necessary, release antibiotics triggered locally by the infection itself, respectively. The inner polymer is anionic (negatively charged) and grafted by one end to a biomaterial such as a polymeric catheter or metal implant. Many antibiotics (e.g., tobramycin) and antimicrobial agents are either cationic or contain amine groups; therefore these small molecules are electrostatically attracted to the inner brush. These agents remain sequestered at physiological pH (i.e., the normal range of pH of blood is 7.35 to 7.45). The loading of the agent scales with the length of the polyanionic brush. As pH decreases, the charge on the anionic brush is reduced and the agent is no longer strongly attracted to the inner brush layer. Because bacterial infection produces a high local acidity and concurrent reduction in pH, these trapped agents are released only near an infected area. Earlier studies show that local pH values as low as 3 can be observed in biofilms. The outer brush layer is a cationic polymer which is grafted at multiple sites along its backbone to the anionic inner brush layer. The cationic polymer serves three purposes. First, this cationic layer is itself antibacterial via contact killing and adhesion reduction. Second, at physiological pH, the outer positively charged bush is collapsed forming a dense layer that further prevents the agents located in the inner brush from releasing. As pH decreases due to local infection, the cationic polymer undergoes extensive swelling (e.g., up to 900×) allowing for release of the sequestered agents. This release is localized near the infected area. A third function of the outer layer is to further shield the hidden agents in the inner brush from the environment thus reducing bacterial resistance due to unnecessary exposure.

FIG. 1A shows the interaction between the polymer bilayer and bacteria during the bacterial attachment, biofilm growth and detachment phases. During initial attachment, the outer layer provides a first stage of defense by preventing bacteria from adhering and/or killing adherent bacteria on the surface. Secondly, if bacteria colonize and biofilm grows on the surface (II, Biofilm), the pH-responsive nanoengineered brushes locally release antimicrobial agents (dashed arrows) to kill bacteria which then detach from the surface (III, Detachment), as pH decreases in the infected area.

Figure 2:
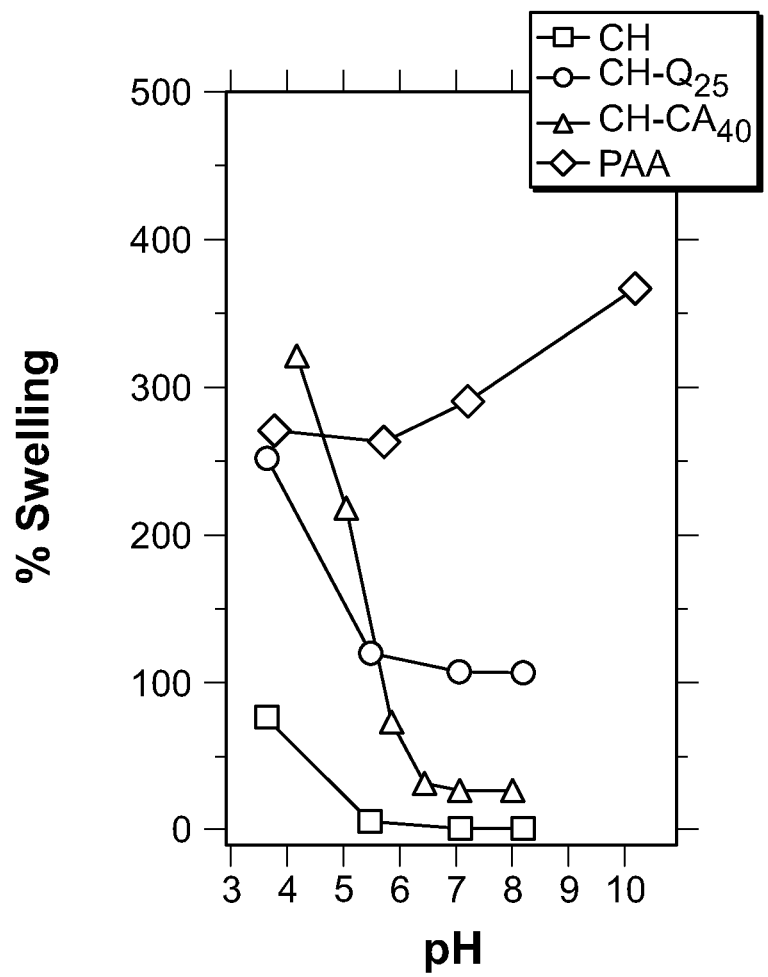
FIG. 2. Percent swelling of CH, modified CH's (CH-$Q_{25}$ and CH-$CA_{40}$), and PAA layers grafted on $SiO_2$ surfaces relative to dry thickness. Biofilm formation produces a local decrease in pH.

Potential polymers for the bilayer are now discussed. For the end-grafted anionic inner polymer layer (FIG. 1B), a poly(acrylic acid) (PAA) brush is an attractive candidate because it can be negatively charged and therefore electrostatically attract cationic antimicrobial agents, such as tobramycin. The PAA brush can be grafted to the surface using surface initiated atomic transfer radical polymerization (SI-ATRP) and characterized by contact angle, dry and in situ spectroscopic ellipsometry, SE. FIG. 2 shows that the PAA brush swells by about 275% relative to the dry thickness at low pH (below ~6) and 375% at high pH (above ~6). Thus, cationic antimicrobial agents in acidic solution (pH=4) can be loaded in the PAA brush (pKa=~6.5) because of electrostatic ionic crosslinking and can be stabilized in the PAA brush by near neutral pH solution (pH=7; without cationic antimicrobial agents) due to more stable ionic-crosslinking by the increased concentration of carboxylate anion groups in PAA brush and then released under acidic solution (pH 4; without cationic antimicrobial agents). For the outer polymer, chitosan (CH), and modified chitosans containing quaternary ammonium salts (CH-Q) and carboxylic acid (CH-CA) are candidate polymers because the core polymer, namely chitosan, is a cationic polysaccharide with inherent antibacterial and biocompatible properties. We have previously shown that grafted layers of CH, CH-Q, and CH-CA are antibacterial, biocompatible, and exhibit pH-dependent swelling properties. In particular, CH, CH-$Q_{25}$, and CH-$CA_{40}$ monolayers layers contract at high pH (above ~7) and swell at low pH (below ~7) as shown FIG. 3. At pH 7, CH, CH-$Q_{25}$, CH-$CA_{40}$ layers are thin and relatively rigid (FIG. 1B). Upon decreasing pH, these three brushes swell from ~0 to 75%, 25% to 325%, and 100% to 250%, respectively. Thus, these polymers allow for selective tuning of the swelling capacity of the outer layer.

Figure 3:
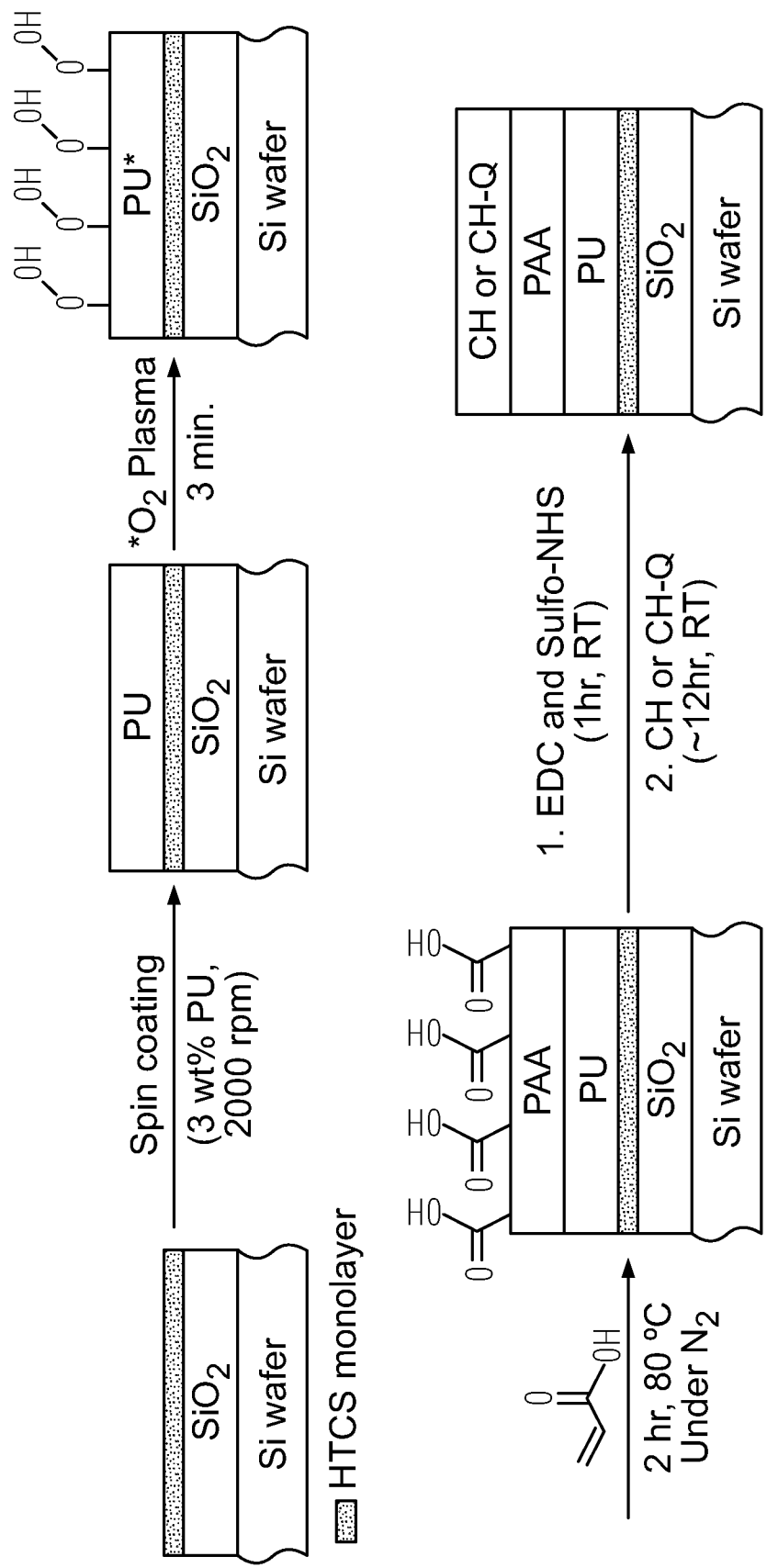
FIG. 3. The experimental scheme for immobilizing CH or CH—X (X=quaternary ammonium salts ($Q_{25}$ or $Q_{50}$) or carboxylic acid ($CA_{40}$)) on PU surfaces via surface initiated radical polymerization of acrylic acid (AA).
Figure 4:
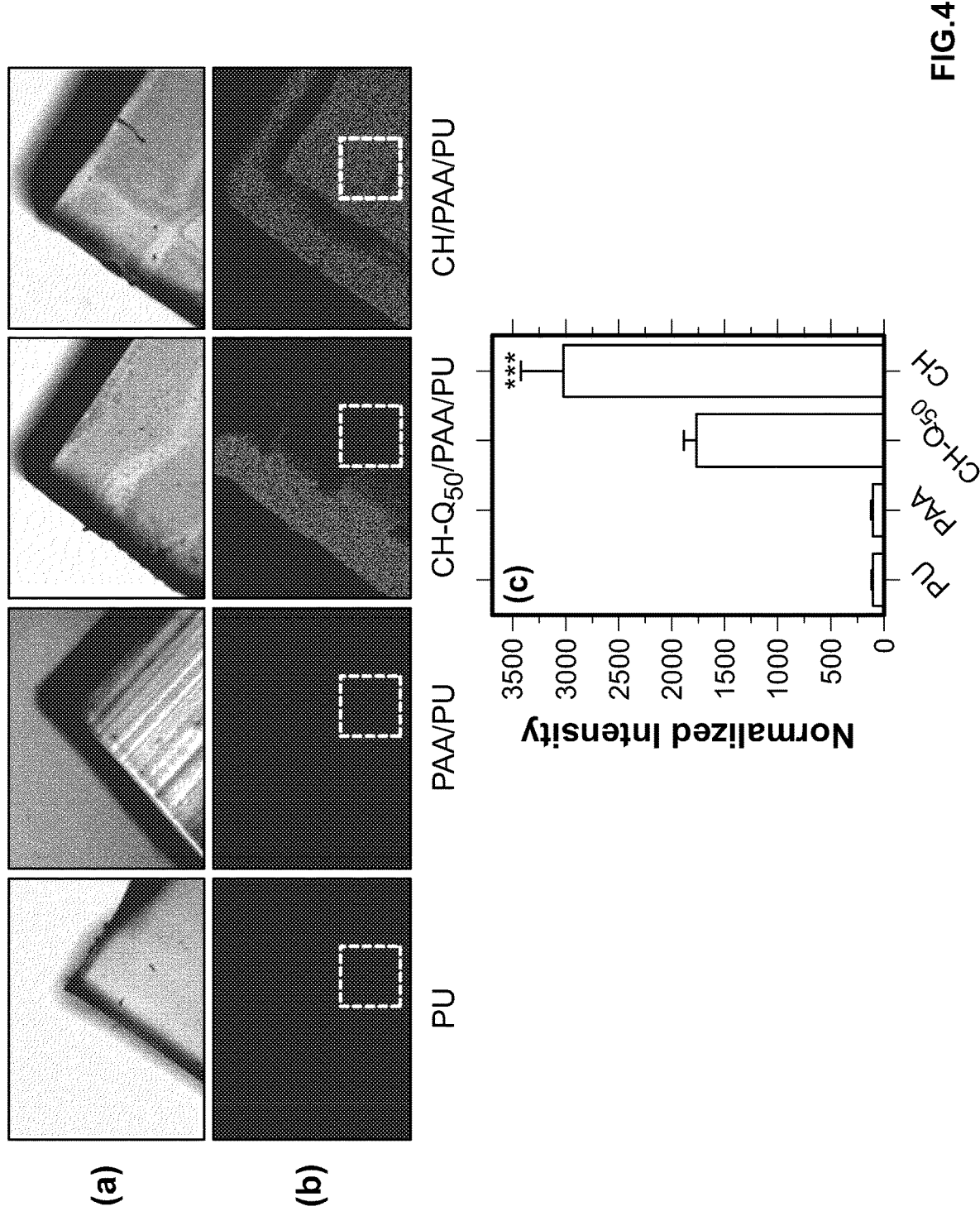
FIG. 4. Bright field (a) and fluorescent images (b) of Rhodamine red treated PU, PAA/PU, CH-$Q_{50}$/PAA/PU, and CH/PAA/PU tubes, respectively. (c) Normalized intensities from fluorescent images of PU, PAA/PU, CH-$Q_{50}$/PAA/PU, and CH/PAA/PU tubes. Data are presented as mean±standard deviation (n=4, square area=70×70 μm$^2$). Statistical significance: ***P<0.0008 versus PU, PAA/PU, and CH-Q/PAA/PU.
Figure 5:
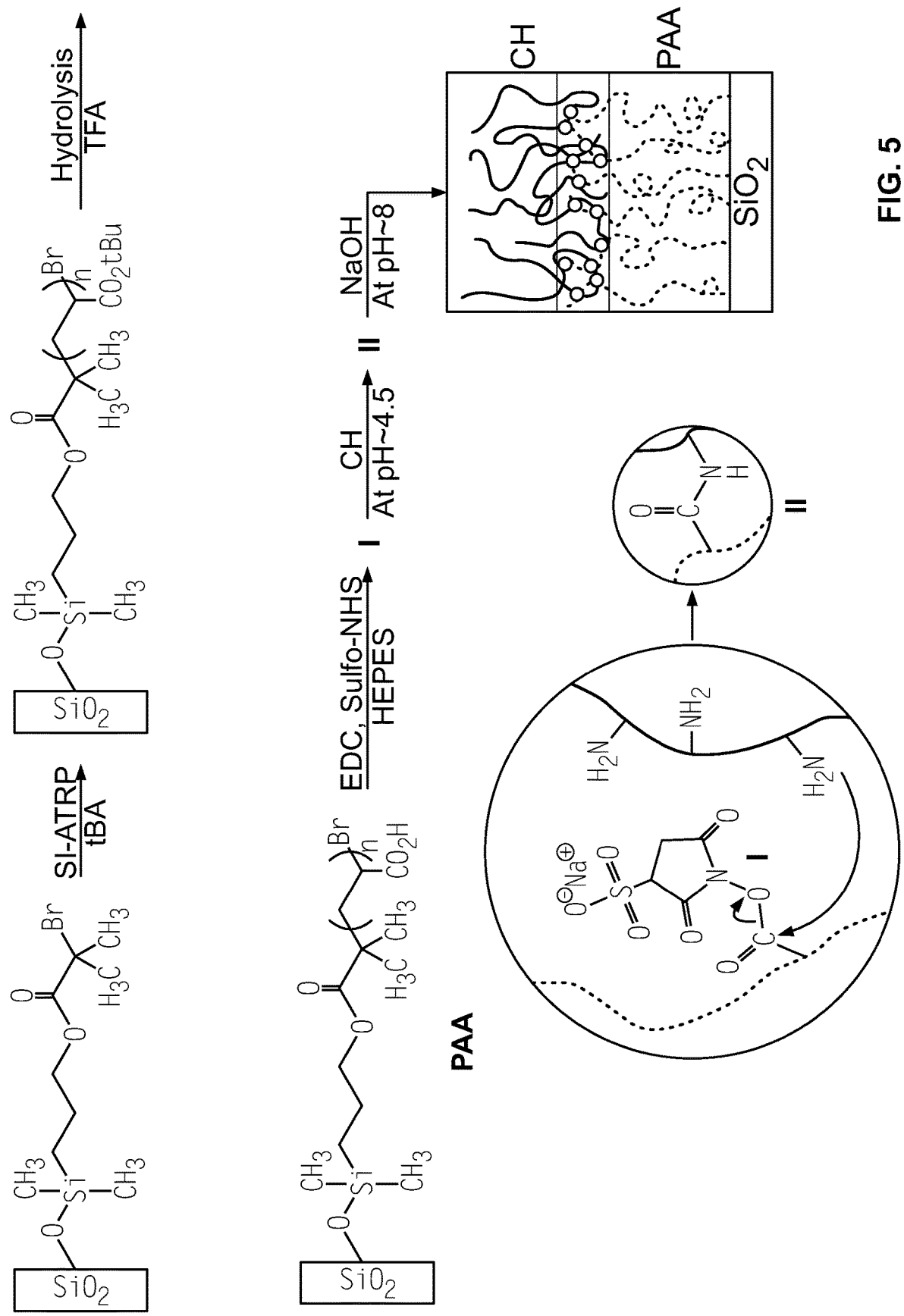
FIG. 5. Scheme for surface-initiated ATRP of tert-butyl acrylate (tBA) and hydrolysis of PtBA polymer brush, followed by grafting CH onto PAA brush via Sulfo-N-hydroxysuccinimide ester funtionalization of acrylic acid of PAA brush. Bottom row, far right: The final bilayer system consists of an end-grafted PAA layer, a middle cross-linked region and an outer CH brush.
Figure 6:
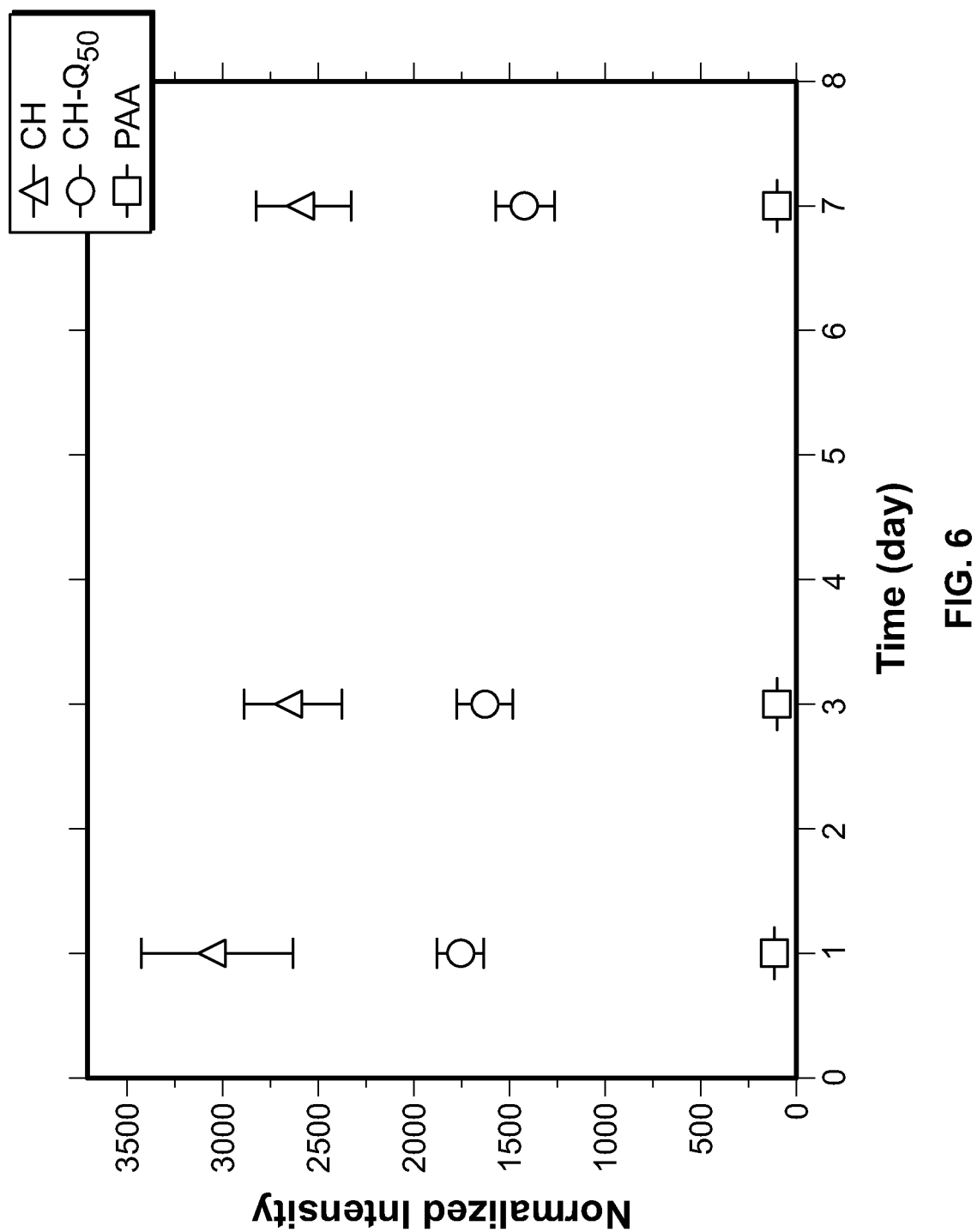
FIG. 6. Material wear testing of rhodamine red labeled CH/PAA/PU and CH-$Q_{50}$/PAA/PU tubes. PAA/PU tube as a control is used.
Figure 7:
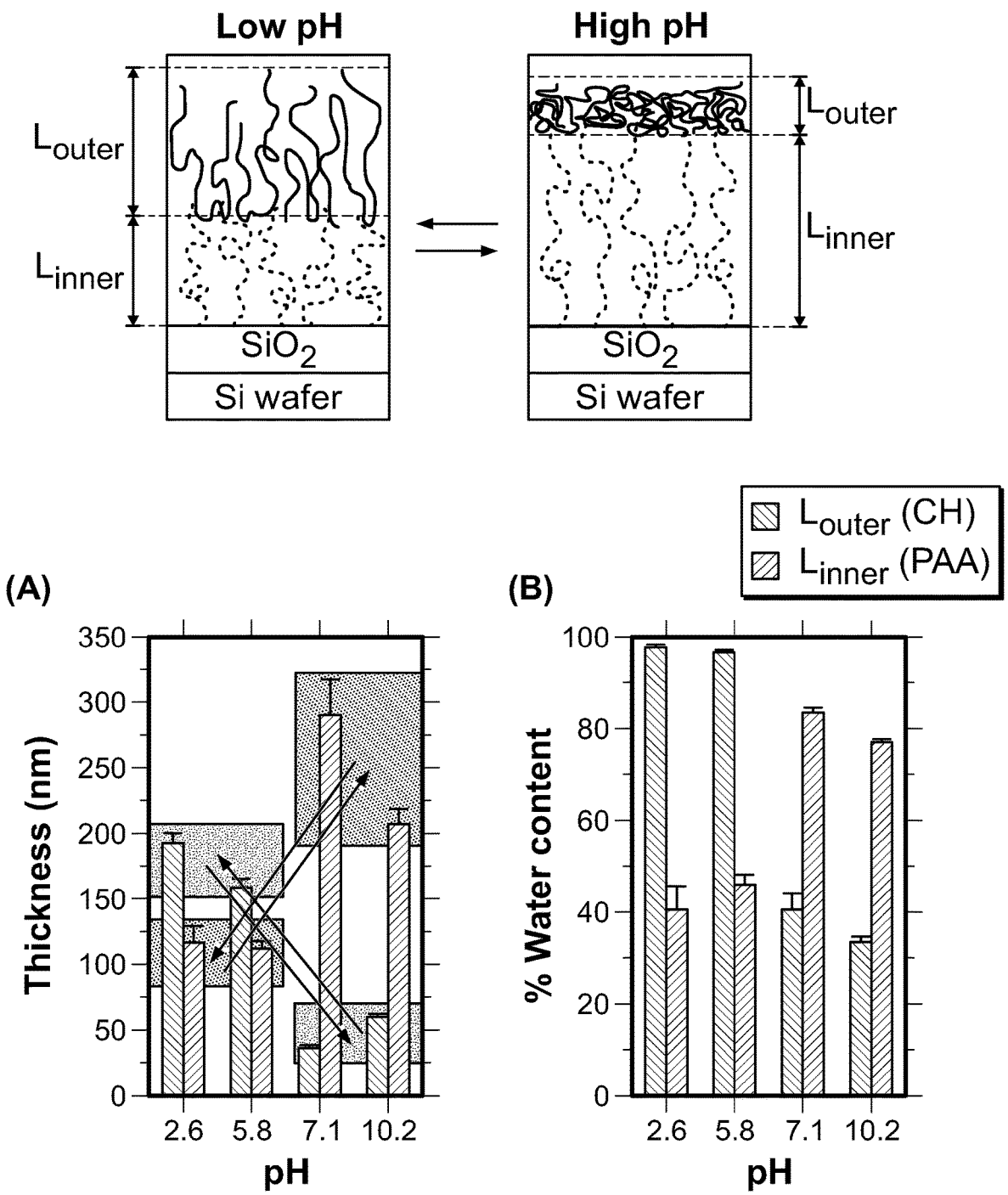
FIG. 7. In situ SE measurements of the total brush thickness (A) and percent water content (B) for the CH/PAA bilayer as a function of solution pH. The bars hatched diagonally from lower left to upper right show swelling of PAA at high pH and collapse at low pH. The bars hatched diagonally from upper left to lower right show collapse of CH at high pH and swelling at low pH. In (A) the double arrows represent the reversible pH response of CH and PAA.

To prepare a bilayer of CH and PAA (FIG. 1) and evaluate bilayer stability, PAA brushes are first end grafted to silicon oxide or polyurethane surfaces and then the acrylic acid groups undergo ester functionalization via sulfo-N-hydroxysuccinimide which react with the amine functional groups of chitosan (FIGS. 3, 4, 5). Each layer was characterized by contact angle, dry and in situ SE as well as fluorescent microscopy. The stability of CH/PAA layer on PU was evaluated using material wear test (FIG. 6). FIG. 7 shows the in-situ SE results for the CH/PAA bilayer. First, upon increasing the pH from 5.8 to 7.1, the thickness (FIG. 7A) and water content (FIG. 7B) for the outer CH layer decreases from 158±8 nm to 37±2 nm, and 96% to 40%, respectively; in contrast, the inner PAA brush layer thickness and water content increases from 113±5 nm to 290±27 nm and 46% to 83%, respectively. For both layers, swelling and contraction are completely reversible and can be tuned by changing the pH of the solution. Because the swelling/contraction behaviors of each layer are complementary, the CH/PAA bilayer is a model system for evaluating the loading of an antibiotic.

Figure 8:
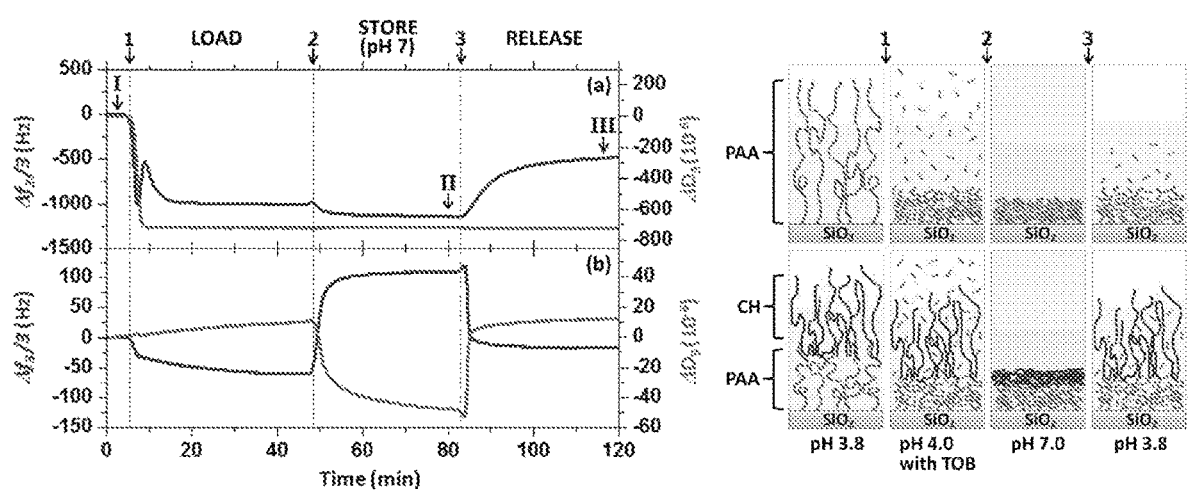
FIG. 8. Traces of Df3/3 (solid line) and DD3 (dashed line) of PAA (A) and CH/PAA (B) vs time as a function of sequential changes in solution pH. Arrows 1, 2, and 3 represent the change from pH 3.8 to pH 4.01 (with TOB), pH 4.01 (with TOB) to pH 7.0, pH 7.0 to pH 3.8, respectively (pH 3.8 and pH 7.0 of the aqueous medium were adjusted by addition of 0.1 N HCl and 0.1 N NaOH under salt-free conditions; pH 4.01 was prepared by adding 10 μL of 1N HCl in 0.3 mM Tobramycin solution (40 mL)). Arrow I, II, and III represent the time points at which the films were dried and thicknesses measured as given in FIG. 9.

Tobramycin (TOB) loading at low pH, storage at pH 7 and release at low pH (FIG. 1B) in PAA and CH/PAA layers were studied using in-situ quartz crystal microbalance with dissipation (QCM-D). FIG. 8 shows the QCM-D results for PAA and CH/PAA layers upon changing the pH solutions. First, a baseline of 0 is established at pH 3.8 (Region I). Then TOB is introduced at nearly the same pH, 4.01 (arrow 1 in FIG. 8). Correspondingly, the frequency, $\Delta f_3/3$, and damping, $\Delta D_3$, of the PAA brush decreases (FIG. 8A) indicating that the mass of the PAA brush increases and PAA behaves like an elastic layer. The former is attributed to the uptake of TOB whereas the latter reflects the crosslinking of the carboxylate anions on the PAA brush by the multi-cationic TOB molecules. This phenomenon is similar to the crosslinking of a chitosan brush by a multi-anion such as a triphosphate anion. When the pH increases from 4.01 to 7.0 (arrow 2), $\Delta f_3/3$ shows a slight decrease whereas $\Delta D_3$ remains constant. This behavior shows that the TOB concentration does not release near physiological conditions, pH 7.0. Upon decrease of the pH from 7.0 to 3.8 (arrow 3), $\Delta f_3/3$ increases rapidly over the initial 30 min and then more slowly. This increase shows that TOB is gradually released at low pH.

The QCM-D behavior for the bilayer brush of CH/PAA is shown in FIG. 8B. The TOB loading step (arrow 1 FIG. 8B) is similar to that of PAA brush (arrow 1 FIG. 8B), although much smaller in magnitude. However, the other steps (pH changes) are difficult to interpret because the pH-dependent swelling properties of each layer confound the interpretation of the frequency increase when increasing pH to 7.0 (step 2) and decreasing pH back to 4.0 to release TOB (step 3).

To address this problem, a quantitative QCM-D method was developed to determine the uptake of TOB by the PAA and CH/PAA brush layers by drying the films at time points corresponding to I, II, and II in FIG. 8. An additional time point corresponding to pH 3.8 and 12 hr is denoted as IV. For regime II (loading of TOB), FIG. 9 and Table 1 show that the areal masses (at pH 7.0) after the uptake of TOB by PAA and CH/PAA layer are 17,231±236 ng/cm$^2$ and 1865±38 ng/cm$^2$, respectively. We attribute the 10× decrease in loading of TOB in CH/PAA to the reduction in carboxylic acid groups available for binding TOB. The loading can be increased by reducing the crosslinking of CH into the PAA layer. Upon decreasing pH to 3.8 for 30 min in order to release TOB (regime III), the areal masses of PAA and CH/PAA layer decrease by 33% and 36%, respectively. These results indicate that the CH/PAA bilayer is a candidate for providing a two-step defense against bacterial adhesion and biofilm formation.

Bilayer Chemistry

Modified chitosan with carboxylic acid (CH-CA) and chitosan (CH) have been immobilized on silicon oxide surfaces via the reaction of primary amines with epoxide functional groups of surfaces. Directly relevant to this disclosure, CH and CH-Q were grafted onto PAA brushes on silicon oxide and/or polyurethane (PU) surfaces using two methods. In the first method (FIG. 3), a film of PU was deposited on a silicon wafer and then activated by exposure to an $O_2$ plasma for 3 min. The PAA brush was grown from the surface by radical polymerization of 30 wt % acrylic acid at 80° C. for 2 hr under $N_2$. To prepare the top CH, or CH-Q brush on the inner PAA layer, the PAA layer was reacted via an EDC-mediated condensation with sulfo-NHS and HEPES at RT for 1 hr. The succinimidyl ester functionalized PAA samples were immersed in 2 wt % aqueous solutions of CH and CH-Q for 12 hr, respectively. In the second method (FIG. 5), monodisperse PAA brushes with high molecular weights were prepared using surface-initiated ATRP of tert-butyl acrylate (tBA) followed by the hydrolysis of PtBA to PAA. The CH brush was grafted onto the PAA brush via sulfo-N-hydroxysuccinimide ester functionalization of acrylic acid followed by quenching the reaction with NaOH solution (pH~8).

Bilayer Characterization

The thicknesses of dry bilayers on planar surfaces were measured by alpha-SE ellipsometer. According to SE results of dry CH/PAA layer, dry thickness and reflective index of CH layer (layer 2) were 13±1 nm and 1.478±0.013 and dry thickness and reflective index of PAA layer (layer 1) were 52±2 nm and 1.533±0.005, respectively. Contact angles were measured by using a 1 µL sessile drop method. For fluorescence microscope experiments, CH and CH-Q coatings on PAA/PU tubes were fluorescently labeled with Rhodamine-Red using a succinimidyl ester to attachment (FIG. 4). The normalized fluorescent intensities of rhodamine red labeled CH and CH-Q grafted to the PAA/PU tubes were 1763±120 and 3029±394, respectively. The CH

TABLE 1

TOB uptake and release in PAA and CH/PAA brushes as a function of pH change.

| | $I_{dry, in\ air}$ Baseline at 0 | $II_{dry, in\ air}$ Loaded TOB | | $III_{dry, in\ air}$ Residual TOB | | | $IV_{dry, in\ air}$ Residual TOB | | |
|---|---|---|---|---|---|---|---|---|---|
| | | Areal mass* (ng/cm$^2$) | molecule/ nm$^2$ | Areal mass* (ng/cm$^2$) | molecule/ nm$^2$ | % Releasing TOB | Areal mass* (ng/cm$^2$) | molecule/ nm$^2$ | % Releasing TOB |
| PAA | | 17231 ± 236 | 222 | 11563 ± 122 | 149 | 33 | 9892 ± 176 | 127 | 14 |
| CH/PAA | | 1865 ± 38 | 24 | 1200 ± 60 | 15 | 36 | NA | NA | NA |

*Average values and standard deviations were calculated using three frequency modes, $\Delta f_n/n$ (n = 3, 5, 7)

Figure 10:
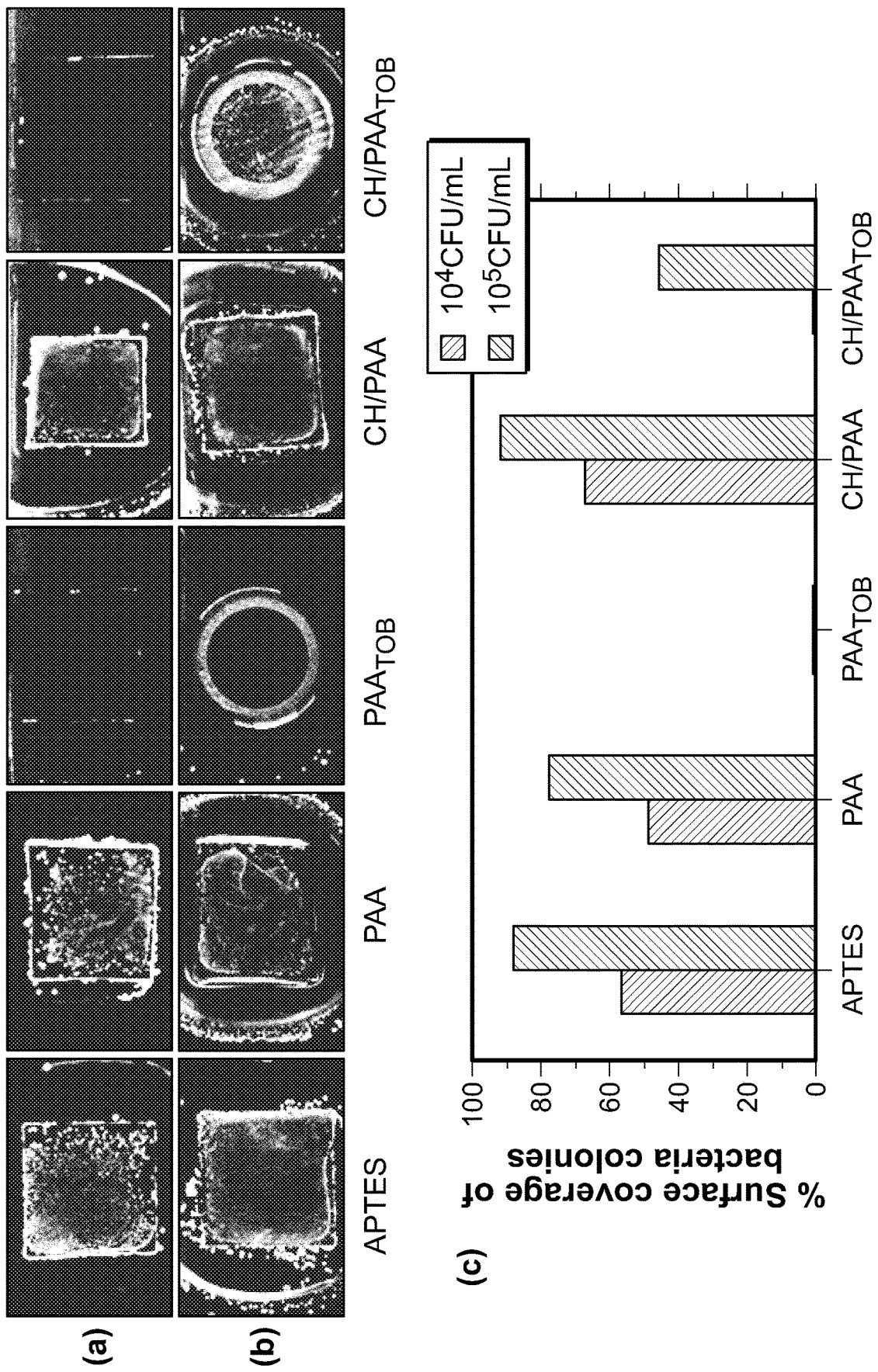
FIG. 10. (a) and (b) rows of optical photographs of bacterial colonies on APTES, PAA, PAA$_{TOB}$ (222 TOB molecules/nm$^2$), CH/PAA, and CH/PAA$_{TOB}$ (24 TOB molecules/nm$^2$) after exposure of ~10$^4$ and ~10$^5$ CFU/mL bacteria solutions, respectively. (c) The graph represents % surface coverage of bacteria colonies estimated using optical images and Image J.

To determine the ability of TOB loaded bilayer brush to kill adherent bacteria via TOB release, the bacterial colony formation on each surface was studied after exposure of bacterial solutions to 3-aminopropyl-triethoxysilane (APTES) modified surface (as a control), PAA layer, TOB loaded PAA (PAA$_{TOB}$) layer, CH/PAA layer, and TOB loaded CH/PAA (CH/PAA$_{TOB}$) layer, respectively. FIG. 10 (a) shows that PAA$_{TOB}$ and CH/PAA$_{TOB}$ layers did not show any bacterial colonies when compared to the others after exposure of a concentrated bacterial solution (*S. aureus* ATCC 25923, 10$^4$ colony forming units/mL (CFU/mL)). The results clearly show that TOB release is effective in killing bacteria.

coating exhibited a higher fluorescent intensity than CH-Q because CH has more primary amine functional groups, which react with succinimidyl easter of rhodamine red label. The pH-dependent swelling properties of polymer layers were measured by in-situ QCM-D and in-situ SE (FIG. 2). For material wear tests, the fluorescent red labeled CH and CH-Q tubes was immersed in fresh saline solutions with shaking at 40 rpm. The normalized intensities of fluorescent labeled CH and CH-Q tubes after shaking for 7 days did not significantly change as shown in FIG. 7. This result demonstrates that the grafted CH and CH-Q are stably grafted onto PAA/PU tubes.

Bilayer Films for a Two-Step Defense

First, the pH-swelling properties of the CH/PAA bilayer were evaluated using in-situ spectroscopy ellipsometry. In-situ SE measurements (FIG. 6) showed that CH/PAA polymer bilayer was chemically stable over a wide range of pH values and each layer exhibited fast, fully reversible pH-dependent swelling and contraction (i.e., thickness changes). A unique characteristic of the CH/PAA bilayer is that each layer exhibits complementary pH-dependent swelling behaviors (FIG. 7). As shown in FIG. 7, at physiological pH, the thickness and water content in the PAA brush (inner layer) is much greater than the collapsed CH layer (outer layer). The collapsed CH can prevent the release of microbicidal agents buried in the inner brush layer (FIG. 1B) and provide a buffer between the agent and environment. As the pH is reduced to 5.8 or 2.6, the inner PAA brush (FIG. 7, bars hatched diagonally from lower left to upper right) contracts while the outer CH layers (FIG. 7, bars hatched diagonally from upper left to low right) swells. As a result, the agent in the PAA can be released from PAA and is able to diffuse through the swollen CH layer.

Figure 9:
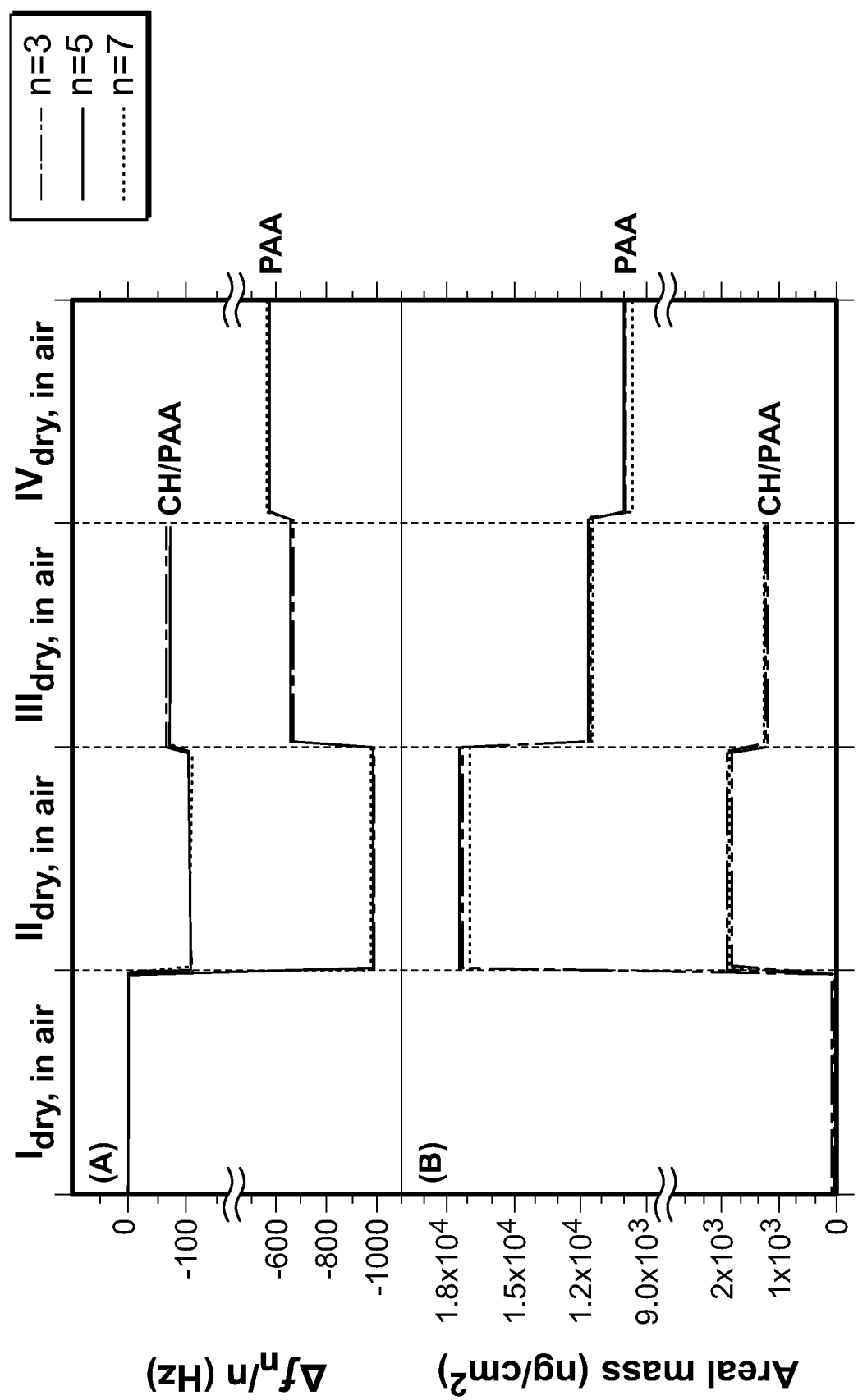
FIG. 9. (A) $\Delta f_n/n$ (n=3, 5, 7) of the dried PAA and CH/PAA bilayer measured using the experimental procedures below. Regime $I_{dry, \ in \ air}$: The samples were dried using $N_2$(g) after exposure of pH 3.8 for 30 min. $II_{dry, \ in \ air}$: The samples (from I) were exposed to pH 4.01 (with TOB) for 30 min, followed by exposure of pH 7.0 for 30 min and drying. $III_{dry, \ in \ air}$: The samples (from II) were exposed to pH 3.8 for 30 min, followed by drying. $IV_{dry, \ in \ air}$: The samples (from III) were exposed to pH 3.8 for 12 hr, followed by drying. The data from regions I, II, III, and IV were combined using Q-soft (Q-Sense). (B) Areal mass (ng/cm$^2$) was measured by using Sauerbrey equation and $\Delta f_n/n$ (n=3, 5, 7) because all dry samples were elastic, thin layers ($\Delta D_n < \sim 2$).

As noted previously, it is difficult to quantify loading and release of TOB using QCM-D because mass increase/decrease is confounded by the swelling/deswelling of the PAA and CH layers. To address this problem, a quantitative QCM-D method was developed to determine the uptake of TOB by the PAA and CH/PAA brush layers by drying the films at time points corresponding to I, II, and III in FIG. 8. An additional time point corresponding to pH 3.8 and 12 hr is denoted as IV. The uptake of Tobramycin (TOB) by PAA and the CH/PAA bilayer is shown in FIG. 9 and Table 1. First, PAA and CH/PAA brush grafted QCM sensors were exposed into pH 3.8 for 30 min, respectively, followed by drying using $N_2$ gas. $\Delta f_n/n$ (n=3, 5, 7) and $\Delta D_n$ of both PAA and CH/PAA were measured in air ($I_{dry,\ in\ air}$ in FIG. 9). For the study of TOB uptake, the PAA and CH/PAA were exposed into pH 4.01 (with TOB) for 30 min, followed by switching from pH 4.01 (with TOB) to pH 7 and dry using $N_2$. $\Delta f_n/n$ (n=3, 5, 7) and $\Delta D_n$ of both PAA and CH/PAA were measured in air ($II_{dry,\ in\ air}$ in FIG. 9). For the study of TOB release at low pH, the TOB loaded PAA and CH/PAA were exposed into pH 3.8 for 30 min, followed by drying using $N_2$. $\Delta f_n/n$ (n=3, 5, 7) and $\Delta D_n$ of both PAA and CH/PAA layers were measured in air ($III_{dry,\ in\ air}$ in FIG. 9). In addition, the samples from III were exposed to pH 3.8 for 12 hr and $\Delta f_n/n$ (n=3, 5, 7) and $\Delta D_n$ of both PAA and CH/PAA layer were measured in air ($IV_{dry,\ in\ air}$ in FIG. 9). The data from regions I, II, III, and IV were combined using Q-soft (Q-Sense). Areal mass (ng/cm$^2$) was measured by using Sauerbrey equation and $\Delta f_n/n$ (n=3, 5, 7) because all dry samples were elastic, thin layers ($\Delta D_n$ <~2). As a result, we observed the uptake amount of TOB by PAA and CH/PAA and percentage releasing of TOB by pH change as we proposed CH/PAA bilayer for TOB loading (at low pH), storage (at physiological pH), and release (FIG. 1B).

Antibacterial Studies of Bilayers (CH/PAA) Loaded with Tobramycin (TOB)

The ability of TOB loaded PAA and CH/PAA brushes to release TOB and kill adherent bacteria was determined. Two different concentrated bacterial solutions (S. aureus ATCC 25923, ~$10^4$ and ~$10^5$ colony forming units/mL (CFU/mL)) were exposed to two APTES surfaces (as a control), two PAA layers, two PAA$_{TOB}$ layers (222 TOB molecules/nm$^2$), two CH/PAA layers, and two CH/PAA$_{TOB}$ layers (24 TOB molecules/nm$^2$) in incubator with humidity for 2 hr, respectively. Percentage surface coverage of bacteria colonies, visualized by colony formation under a thin film of TSB agar (in incubator overnight), was estimated using image J (FIG. 10). As shown in FIG. 10(c), at the bacterial concentration ($10^4$ CFU/mL), percentage surface coverage of S. aureus colonies on APTES, PAA, and CH/PAA layers showed 57%, 48%, and 67% respectively. As the exposed bacterial concentration increased (from $10^4$ to $10^5$ CFU/mL), percentage surface coverage of S. aureus colonies on APTES, PAA, and CH/PAA layers increased to 88%, 77%, and 92%, respectively. In contrast, S. aureus colonies were not observed on PAA$_{TOB}$ surfaces after the exposure of both concentrated solutions. This result represents that TOB amount loaded in PAA$_{TOB}$ layers (222 molecules/nm$^2$) was enough to kill adherent bacteria on the surfaces via TOB releasing at both bacterial concentrations. In the case of the CH/PAA$_{TOB}$ layer, S. aureus colonies were not observed on CH/PAA$_{TOB}$ surfaces after the exposure of the lower concentrated solution ($10^4$ CFU/mL). However, the percentage surface coverage of S. aureus colonies on CH/PAA$_{TOB}$ layer at the higher concentrated solution ($10^5$ CFU/mL) was 46%. It represents that TOB amount loaded in CH/PAA$_{TOB}$ layers (24 molecules/nm$^2$) was enough to kill adherent bacteria via TOB releasing at the lower concentrated solution ($10^4$ CFU/mL) rather than the higher concentration ($10^5$ CFU/mL); the TOB amount loaded in CH/PAA$_{TOB}$ layers has a threshold for killing adherent bacteria via TOB releasing at a specific bacterial concentration. The overall results clearly show that TOB release is effective in killing bacteria (or at least keeping them from sticking to surface after a given time). As the TOB amount loaded in the layer is higher, the layer has more bactericidal efficiency even at higher bacterial concentration.

One can vary the reaction conditions for crosslinking the CH onto/into the PAA inner layer because TOB adsorption depends on the availability of carboxylic acids that are involved with covalent cross linking as shown in the bottom row of FIG. 5. For low, medium and high cross-linking, one can evaluate loading of TOB in the polymer bilayer at low pH, the retention of TOB near pH~7, and release of TOB as pH decreases. Studies may include in-situ QCM-D, in-situ AFM, neutron reflectivity (NR), and other methodologies. For the different TOB loaded amounts tuned by controlling molecular weights of PAA inner layer and crosslinking reactions the CH onto/into the PAA inner layer, in vitro bactericidal efficiency at different bacterial concentrations can be evaluated. In vivo antibacterial testing over a range of pH exposures relevant to vascular biology, bioimplant utilization and other industrial applications can be performed. In order to make new multifunctional bilayers outer layer can be varied to include, for example, copolymers of CH-CA and CH-Q.

Example 2

Nanoengineered Coatings for Preventing Catheter Related Bloodstream Infections

Nanoengineered grafted polymer brushes can prevent/inhibit catheter related bloodstream infections (CRBSI) via a novel two-step defense mechanism. Specifically, surfaces are tested for their ability to resist the initial stage of infection, namely preventing bacteria from forming molecularly specific bonds with the surface. Secondly if bacterial colonization and biofilm formation does occur, the nanoengineered brushes can locally release antimicrobial agents near the infection. Two systems are investigated. A brush of chitosan or modified chitosans containing quaternary or carboxylic acid groups are directly grafted to planar and tubular polyurethane via a short silane linker. Our research shows that these films grafted to model hard surfaces (e.g., glass or silicon) exhibit unique pH dependent swelling properties that inhibit bacteria attachment and retard biofilm formation. These model studies can be translated from hard planer surfaces to polyurethane films and tubes, while retaining outstanding antimicrobial properties. A bilayer grafted to polyurethane can provide improved loading and release capabilities compared to the monolayer of (modified) chitosan. Here we replace a short silane linker with a poly(acrylic acid) (PAA) brush end-grafted to polyurethane that can serve as a reservoir for aminoglycoside antibiotics that releases biofilm forms and reduces pH.

For the monolayer and bilayer brush, the swelling behavior on polyurethane is investigated, as well as key properties such as surface charge, modulus and morphology. The ability of the brushes to load drug, retain drug near pH~7, and release drug as pH decreases is investigated for both technologies.

The Center for Disease Control and Prevention Report (2007) noted that there were 1.7 million healthcare-associated infections in the US. Of these, 14% were bloodstream infections. CRBSI can be dramatically reduced by preventing bacterial colonization through nanoscale modification of the surface of polyurethane vascular catheter. CRBSI is characterized by bacterial adhesion on indwelling vascular lines, followed by formation of a biofilm that anchors bacteria to the catheter surface. Once a biofilm forms, bacteria are 1000 times more resistant to antibiotics than planktonic bacteria. Two of the major bacterial offenders, *S. aureus* and gram-negative *bacilli* (e.g. *P. aeruginosa*) are investigated. Tobramycin was chosen as the antibiotic because it is active against both *S. aureus* and *P. aeruginosa*, and contains appropriate functional groups for loading and releasing from (modified) chitosan and poly(acrylic acid).

The bilayer system is a significant departure from competing technologies involving immersion, coating or covalent grafting of antibiotics. The bilayers described herein are adaptable to the broader biomaterials industry where infections on implants and other devices are prevalent.

Technical Project:
 Objectives.

The nanoengineered grafted polymer brushes prevent catheter related bloodstream infections (CRBSI) via a novel two-step defense mechanism. Specifically, surfaces are tested for their ability to resist the initial stages of infection by preventing bacteria from making molecularly specific bonds with the surface. Secondly if bacterial colonization and biofilm formation does occur, the nanoengineered brushes can locally release antimicrobial agents near the infection. In part, this technology is described in PCT patent application publication WO 2012/109239 entitled "Multifunctional Chitosan Grafted Surfaces and Uses Thereof," incorporated by reference herein in its entirety, which describes the chemistry and properties of modified chitosan brushes that are protein and bacteria resistant (See FIG. 1). The first objective is to translate fundamental research on chitosan (CH), quaternary modified CH (CH-$Q_n$, n=% substitution) and carboxylic acid modified CH (CH-CA) brushes from hard planer surfaces to polyurethane films and tubes, while retaining outstanding antimicrobial properties. Here, an antimicrobial is a substance that kills or inhibits the growth of microorganisms such as bacteria. A second objective is to demonstrate that a bilayer grafted to polyurethane improves antimicrobial loading and release capabilities compared to the monolayer of (modified) chitosan. Here we use a poly(acrylic acid) (PAA) brush end-grafted to polyurethane. The anionic PAA not only bonds the polyurethane with the top (modified) chitosan layer, but also serves as a reservoir for antimicrobials that release upon a reduction in pH due to biofilm formation. Because subinhibitory concentrations of antibiotics can activate biofilm formation, the bilayer has an advantage over the monolayer because antibiotics are shielded from bacteria until infection occurs.

Technology that Forms the Basis of the Project.

Figure 11:
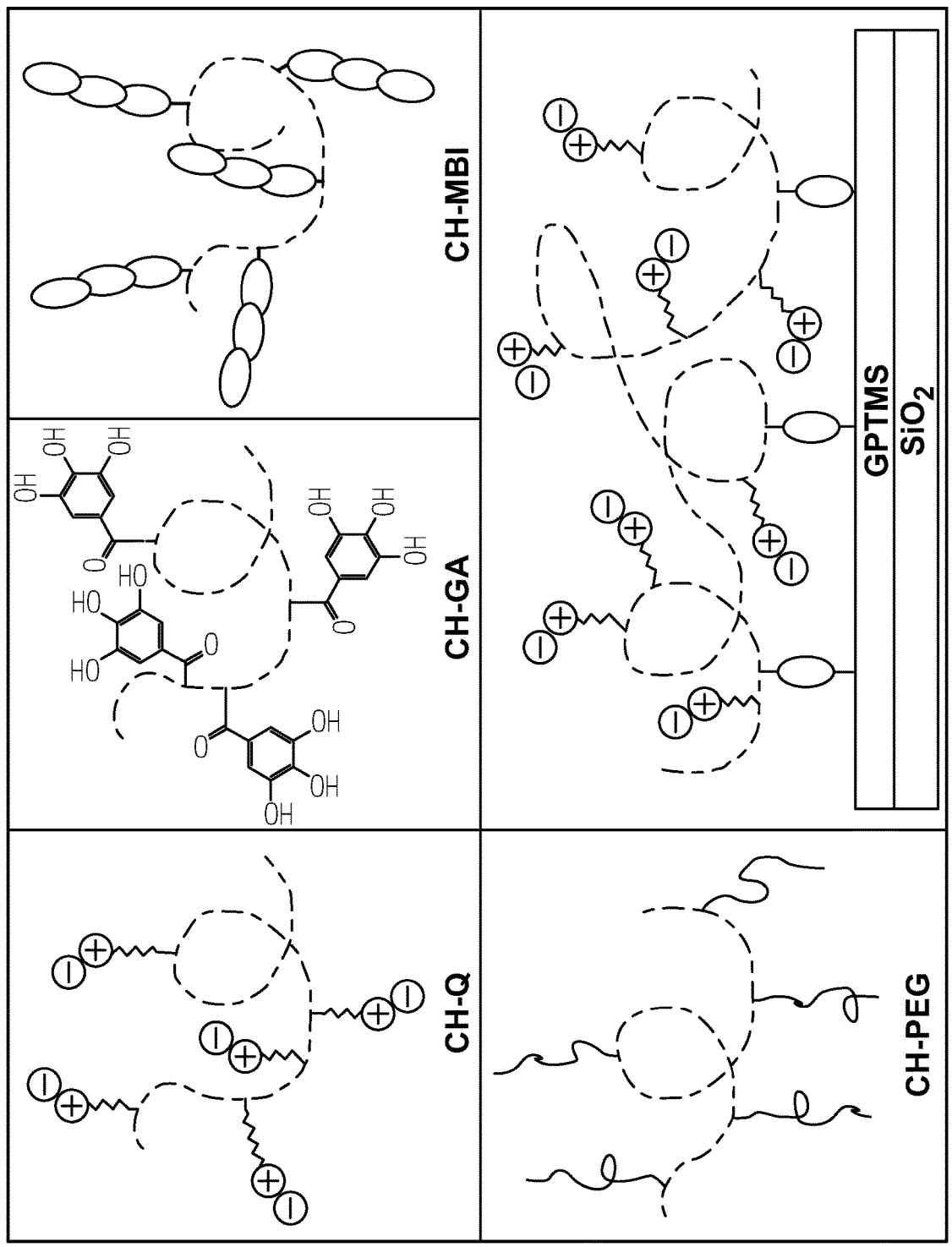
FIG. 11 shows modified chitosan brushes.

A research goal is to translate our capabilities for fabricating infection-resistant, nano-scale surface coatings from model hard substrates to a polymer used for vascular catheters. Our specific approach is to graft monomolecular (modified) chitosan (CH) or a bilayer of CH and PAA that provides a duel defense mechanism against bacterial attachment and biofilm formation via electrostatic repulsion and contact killing via antibiotics, respectively. FIG. 11 shows how our monomolecular brush provides a general platform for antibacterial surfaces.

The technology is based on grafting CH modified with cationic (quaternary ammonium salts, CH-Q), anionic (gallic acid, carboxylic acid), and neutral (PEG) molecules as well as antimicrobials (MBI, Tobramycin). Previously, we have shown that CH-$Q_{50}$ reduces bacterial attachment by 30× relative to glass The second defense mechanism is investigated by covalently grafting or electrostatically binding the aminoglycoside Tobramycin, which is effective against Gram-positive and Gram-negative bacteria.

Nanotechnology underpins both the length scale of the grafted molecules and the tools used to characterize the charge, molecular structure, roughness, and morphology of the surfaces. Planar and tubular polyurethanes can be grafted with a monolayer of CH or a bilayer of CH and PAA with thicknesses ranging ~a few nm to ~100 nm depending on the surrounding pH. The strategy employed is that the CH outer film remains collapsed and smooth at physiological pH. This is an important characteristic because surface roughness of polymers has been shown to promote bacteria adhesion and biofilm deposition. However upon a reduction in pH, chitosan swells to release antibiotics and/or allow for antibiotics from the underlying poly(acrylic acid) to permeate the top chitosan layer. In addition to nanoscale coatings, we have pioneered nanotechnology tools to interrogate molecules and cells using quartz crystal microbalance to study swelling of chitosan brushes as well as cell/bacteria adhesion, single molecule alignment and dynamics on nanocomposite surfaces using AFM-TIRF and nanomechanical properties of cells using AFM-TIRF.

Improved Technology.

Our technology overcomes a major limitation of current devices. The technological approaches below and others that alter surface properties (e.g., surface hydrophobicity/philicity, hydrogel coating), macromolecules in biofluids have had some success in reducing bacterial adhesion. However, many are fouled by rapid adsorption of proteins and glycoproteins which can act as binding ligands for bacteria. Thus, even if bacteria are unable to attach directly to the device, nonspecific adsorption of proteins can mask the underlying structure and prevent antimicrobials from contacting bacteria. Our technology has the inherent advantage of inhibiting protein fouling, while reducing microbial adhesion and impeding biofilm formation.

Advantages of our technology are, for example, (1) the surface is optimized to resist bacterial colonization; (2) antibiotic use is reserved until bacteria have colonized the implant; (3) antibiotics can be loaded at the point-of-care; and (4) antibiotics are only released locally at the site of infection.

Development of these surfaces can minimize the complications and morbidity associated with use of acute-care catheters.

Methods:

This section presents methods and results the demonstrate our expertise with preparing and characterizing chitosan modified surfaces as well as quantifying their antimicrobial properties. The feasibility to transfer results from model systems to catheters is high.

Chitosan Brush Chemistry, Characteristics and Properties

Grafting of Chitosan to Silicon Oxide:

Chitosan (CH) is a naturally occurring linear amino polysaccharide containing β-(1-4)-linked D-glucosamine and N-acetyl-D-glucosamine. The biocompatibility of CH is well-known, and we have extended its utility by grafting CH and its derivatives onto hard and soft surfaces, including polymeric vascular biomaterials. Here we describe the grafting of CH, CH modified with n % quaternary ammonium salts ($CH-Q_n$) and CH modified with 40% carboxylic acid ($CH-CA_{40}$) onto hard surfaces. $CH-Q_n$ and $CH-CA_{40}$ were prepared by a Michael reaction of chitosan with an acryl reagent (AETMAC and acrylic acid) in aqueous solution and the percent substitution quantified by $^1$H-NMR. Although CH is insoluble at pH 7, $CH-Q_{25}$ and $CH-Q_{50}$ are made soluble between pH 3 and 9 by the substitution of quaternary ammonium enabling surface grafting in water rather than organic solvents. This green chemistry is particularly advantageous for device manufacturing. Although insoluble at pH 7, $CH-CA_{40}$ is soluble at pH 6.5 placing it between the CH and $CH-Q_n$. CH, $CH-Q_n$ and $CH-CA_{40}$ were grafted to glass slides and silicon oxide using 3-glycidoxy-propyltrimethoxysilane (GPTMS) as a linker, which can also be used to attach brushes to PU. The amino functional groups from CH react with the GPTMS epoxide groups to produce stable covalent bonds. These results demonstrate that modified chitosans can be covalently and stably grafted. This chemistry is compatible with polyurethane used in vascular and urinary catheters.

Brush Characteristics

Figure 12:
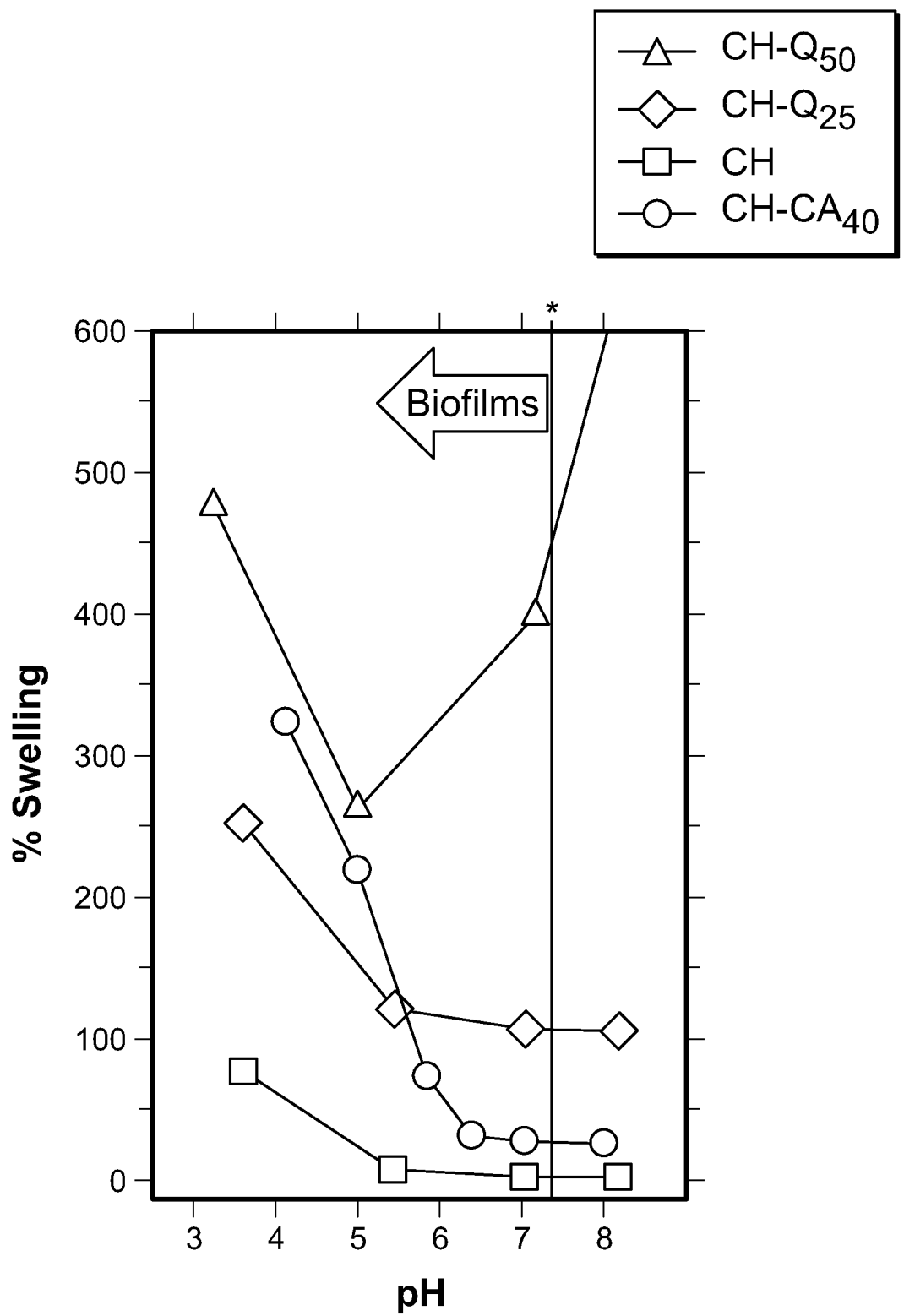
FIG. 12 shows swelling of CH and modified CH's relative to dry thickness. The response shifts to higher pH for CH-$CA_{40}$ brushes.

Surface charge partly determines the amount and conformation of adsorbed proteins. The zeta potential of $CH-Q_{50}$ increases from +39 mV to +49 mV upon lowering pH from 8.2 to 7.30; below pH~7, the zeta potential remains constant at +50 mV because the amino groups have a $pK_a$ of ~7.4. The thickness values of CH, $CH-Q_{25}$ and $CH-Q_{50}$ were determined by in-situ spectroscopic ellipsometry (SE) and quartz crystal microbalance with dissipation (QCM-D). Using QCM-D results, FIG. 12 shows that $CH-Q_{50}$ exhibits a minimum swelling near pH 5 and swells dramatically and symmetrically at higher and lower values, whereas CH and $CH-Q_{25}$ show monotonic with decreasing pH. Recently $CH-CA_{40}$ was synthesized in order to increase the pH at which monotonic swelling is observed while maintaining a collapsed structure near pH 7. $CH-CA_{40}$ is an attractive brush because it collapses above pH 6.5 (drug retention) and swells below pH 6 (drug release). Although beyond the scope, silver nanoparticles can also be loaded into these films to provide antimicrobial properties. Because of their controllable swelling, CH, $CH-Q_{25}$ and $CH-CA_{40}$ brushes are attractive as pH responsive surfaces for reducing bacteria adhesion and loading/releasing drug.

Brush Stiffness:

In addition to QCM-D, brush thickness and modulus will be determined by force spectroscopy to evaluate heterogeneity. We have previously determined the modulus of dextran films as well as the frequency dependent modulus of macrophages. Layer stiffness is an important factor in bacterial adhesion. For example, bacteria strongly attach to collapsed CH whereas CH grafted to swollen poly(acrylic acid) may better resist adhesion.

Cross-linking and Collapse of Chitosan Brushes:

CH, $CH-Q_{25}$ and $CH-CA_{40}$ brushes collapse near pH 7 and swell as pH decreases, attractive attributes for capturing and releasing drug. Because of their cationic groups, chitosans can be electrostatically cross-linked using a multifunctional anionic polymer and/or bind with antibiotics containing anionic groups (e.g., tobramycin). Very recently, we demonstrated that $CH-CA_{40}$ can be cross-linked using $[P_3O_{10}]^{5-}$. At pH 4.1, $CH-CA_{40}$ thickness was 50 nm and, upon adding $[P_3O_{10}]^{5-}$, showed a nearly instantaneous collapse to 15 nm. Upon increasing pH to 7 the thickness decreased slightly to 3 nm and remained cross-linked. Thus, a $CH-CA_{40}$ brush has potential to retain antibiotics at physiological pH and locally release antibiotics as pH is reduced by a biofilm.

Drug Loading and Release from Brushes:

To model drug loading, retention and pH-enhanced release, we have tested Congo Red, Phenol Red and Alizarin Red S as "mock antibiotics" in $CH-Q_{25}$ layers. These compounds were loaded at pH 4 into the swollen brush, which was then collapsed by exposure to $[P_3O_{10}]^{5-}$. Using fluorimetry, the dye was retained at pH 7 and then eluted upon lowering pH. Experiments are needed to test the loading and release of tobramycin in CH, $CH-Q_{25}$, $CH-CA_{40}$ and PAA.

Bacteria Adhesion Strength and Attachment

Antibacterial Surfaces Retard Bacterial Adhesion.

We have previously demonstrated that (a) surface-tethered antimicrobials significantly reduce bacterial colonization and biofilm formation on biomaterial surfaces, (b) adsorbed serum proteins do not alter antibacterial activity, (c) our surfaces maintain efficacy for times far in excess of elution systems, (d) surfaces are biocompatible, and (e) antibacterial surfaces show efficacy in animal models of infection. These studies support our historical interest in anti-infective surfaces and indicate that our plans are feasible for translating basic research into antimicrobial catheters.

CH-Q Inhibits Bacterial Attachment:

*S. aureus* (ATCC™ 35556®, ~$10^4$ cfu/mL) were incubated on $SiO_2$, aminopropyl-triethoxysilane (APTES) modified $SiO_2$ and CH-Q grafted $SiO_2$ under TSB agar. By direct counting, 219±74, 149±77, and 7±5 colonies/cm$^2$ of *S. aureus* were present on the APTES, $SiO_2$, and CH-Q surfaces, respectively. The CH-Q layer had up to ~30× reduction in bacterial attachment relative to the control surfaces. Reduced colonization is attributed to quaternary ammonium interactions with the *S. aureus* membrane.

Figure 13:
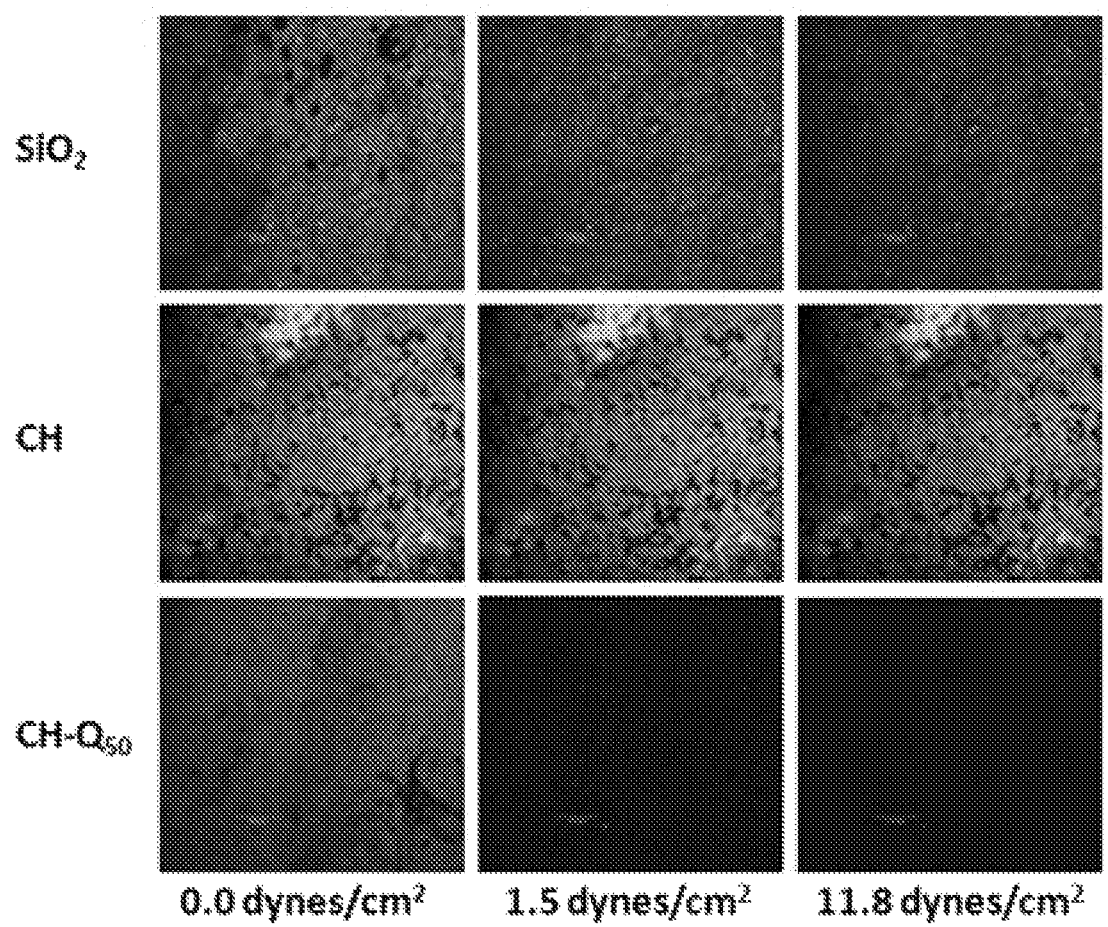
FIG. 13. (a) Confocal microscopy images of bacteria on $SiO_2$, CH and CH-$Q_{50}$ surfaces at shear stress of 0, 1.5 and 11.8 dynes/cm$^2$.

Bacterial Adhesion to Biomaterials:

We assessed adhesion force using our parallel plate flow apparatus. Specifically, biofilm was formed on $SiO_2$ (as a control), CH, and $CH-Q_{50}$ brushes by incubation in *S. aureus* (GFP-expressing AH1710, ~$10^6$ CFU/mL), 2 days, 37° C., pH 7.3. Surfaces were mounted in our custom parallel-plate perfusion chamber attached to a confocal microscope and exposed to shear flow. FIG. 13 shows fluorescent labeled *S. aureus* and bacteria coverage as a function of shear stress. At the highest shear stress (11.8 dyne/cm$^2$), bacterial coverages on $SiO_2$ and CH are ~60% and ~90% respectively. However, on $CH-Q_{50}$, exposure of 1.5 dyne/cm$^2$ removes nearly all bacteria with only ~3% remaining. Large fractions of adherent bacteria detach from the modified chitosan surface at shear stress levels similar to venous blood flow. Surface modulus and swelling can be engineered to yield both low bacterial adhesion strength and low bacterial colonization/proliferation, characteristics designed to reduce biomaterial-related infections.

Bilayer Brushes on Polyurethane (PU)

Another aspect is to have a new antimicrobial system in which the linker itself loads/releases drugs. Here, the chitosans provide the first defense against attachment whereas drug release from the linker initiates as biofilm forms. Poly(acrylic acid) (PAA) is chosen as the linker because it can be readily grafted to PU, attracts aminoglycoside antibiotics and collapses as pH decreases. FIG. 3 shows the sequence of steps to prepare the CH/PAA bilayer on PU. PAA was first grafted to PU using surface initiated radical polymerization (SIRP). Then, the carboxylic acid groups were modified with a succinimidyl ester which react with the amine group of CH (CH-Q). Hydrophilic HTCS was used to prevent dewetting of PU from Si. The dry PAA brush thickness and contact angle were 46 nm and 29°, consistent with literature. The CH and CH-Q layers are 25 nm and 12 nm, and exhibit water contact angles of 25° and 12°, respectively.

The bilayer brush was attached to PU tubes using the chemistry outlined in FIG. 4. To confirm covalent grafting of the PAA brush to PU, the PAA was reacted with a fluorescently labeled peptide via its amine end group (AFC-Arg-Arg-Ala-NH$_2$, AFC-P). The AFC-P grafted on PAA/PU tube exhibited a strong blue fluorescence compared to the controls, namely 2531±108 versus 96±4, and 153±296 for PU and PAA/PU, respectively. Although beyond this proposal, the antimicrobial properties of modified PAA brushes with covalently bound and physisorbed antibiotics are of interest. To demonstrate that chitosan can be grafted to PAA, rhodamine red labeled CH and CH-Q were reacted with the PAA/PU. FIGS. 4a and 4b show bright field and fluorescent microscopy images of PAA/PU, CH-Q/PAA/PU and CH/PAA/PU. Only the chitosan modified surfaces showed significant fluorescence. FIG. 4c shows that the normalized fluorescent intensities support bilayer brush formation. CH has more primary amine functional groups than CH-Q and therefore had a higher fluorescence intensity. This study demonstrates that CH and CH-Q grafted brushes attach to PAA via the primary amine functional groups of D-glucosamine units. To evaluate the bilayer stability on PU tubes, material wear tests were performed. The fluorescence intensities of CH and CH-Q grafted tubes were found to be similar before and after immersion in saline shaken at 40 rpm for 7 days supporting the stability of the bilayer brushes.

CH, CH-Q$_{25}$ and CH-CA brushes that are directly grafted to UR as well as those grafted via a PAA linker can be investigated. Our studies show that CH and CH-Q can be attached to planar and tubular polyurethane. Although CH-CA has not yet been grafted to PUR, the same reaction can be used. The swelling and drug eluting properties of surfaces as well as bacteria/biofilm adhesion can be investigated.

pH-Responsive Brushes and Drug Loading/Elution Profiles.

The purpose is the fabrication and physical characterization of chitosan and chitosans functionalized with either a quaternary ammonium salt or carboxylic acid. These brushes can be either grafted to PUR via a short silane or long poly(acrylic acid) (PAA) linker. The PAA linker also serves as a depot for loading tobramycin (TB), which is active against both S. aureus and P. aeruginosa, common pathogens in CRBSI. The surfaces are designed to be stable at normal physiological conditions (blood pH 7.35 to 7.45), but release drug upon biofilm formation.

Experimental Plan:

Stable chitosan brushes constructs can be evaluated and tailored to create a hierarchy of surface properties that have native (i.e., cationic brush) and active (release of antibiotic) resistance to bacteria. To achieve this, we have devised a novel approach that has the potential to not only encapsulate and release a variety of antibiotics but also can be used at the point of care. One can graft brushes directly to polyurethane or via a poly(acrylic acid) brush and characterize their nano-scale properties (charge, modulus) and structure (roughness), and tobrymycin elution profiles. For the direct attachment, chitosan brushes are exposed to $[P_3O_{10}]^{5-}$ which cross-links and collapses the brush. One advantage of the new bilayer system is that PAA can be loaded with tobramycin at pH 7 w/o cross-linker (see FIG. 6).

Methods:

Brush Grafting and Drug Loading:

The grafting of CH and CH-Q$_n$ and now CH-CA$_{40}$ is well established by our research team. In the monolayer system, our grafted chitosan layers are swollen near pH 4, exposed to tobramycin, exposed to cross-linker, and collapsed near pH 7. FIG. 1 summarizes the new bilayer technology where PAA is the reservoir for loading tobramycin. Note: tobramycin will not load in chitosan at pH 7 unless the chitosan is collapsed with cross-linker. The amount and rate of tobramycin uptake can be monitored using QCM-D.

Characterization:

Nanoscale structure, thickness, viscoelasticity and electrostatic profiles can be determined for each grafted chitosan. Details appear in methods section.

Film Modulus:

The modulus of grafted chitosan is measured by force spectroscopy and QCM-D. An E4 QCM instrument (Q-Sense Inc., Gothenburg, Sweden) can monitor swelling of chitosan as a function of pH. Force spectroscopy determines surface heterogeneity whereas QCM-D averages across the sample (~cm).

Drug Elution Measurement:

One can continuously perfuse surfaces in our parallel plate chamber assembly with PBS solution at pH 7.3, 37° C. using our servo apparatus. The flow rate can be set to keep the shear stress at 1 and 10 dyne/cm$^2$ for up to 48 h to simulate clinical ventilation or blood flow shear conditions. Effluent will be sampled up to 48 h and assayed by HPLC for eluted antibiotic levels.

Antiadhesive and Antibacterial Efficacy of Brushes.

Because the indwelling catheter is exposed to bacteria from the skin these devices are prone to bacterial colonization. The tissue interface of the indwelling catheter is monitored by an attenuated immune surveillance due to the presence of the "foreign body". Our goal is to create devices that withstand these constant assaults over the 1-2 weeks critical for acute care. One can fabricate and characterize coatings that are antibacterial due to (1) surface characteristics of the modified CH brushes and (2) the pH-responsive antimicrobial reservoir from cross-linked CH or the PAA linker layer. One can test the effectiveness of this bio-responsive system against bacterial colonization. Two strains of bacteria can be tested: Staphylococcus aureus (S. aureus, ATCC® 25923™) is a Gram-positive organism that is the most common cause of deep infection; Pseudomonas aeruginosa (P. aeruginosa ATCC® 17933™) is a Gram-negative organism commonly associated with deep infection.

Experimental Plan:

Initially, chitosan films can be tested for anti-bacterial activity under static conditions. Surfaces will be exposed to ~$10^2$ cfu/ml of *S. aureus* or *P. aeruginosa* and surface colonization measured after 6 h, 37° C. Surfaces can be challenged over a 7 day period. After each exposure, the surfaces can be assayed or washed and re-incubated for the next challenge. Only surfaces that show a ≥10-fold decrease in bacterial colonization can be moved forward (Surface S1). Next, the successful S1 surfaces loaded with tobramycin can be tested under static conditions at 37° C. Bacteria ($10^2$ cfu/ml) can be incubated with the S1+ surfaces for 6 and 48 h, 37° C. The planktonic bacteria and adherent bacteria can be determined. S1+ surfaces can also undergo (i) visualization of bacterial colonization, (ii) repeated bacterial challenges for 7 days, and (iii) analysis of material properties after exposure to bacteria.

The combined effect of the antibacterial surface and the depot antibiotics can cause ≥100-fold decreases in bacterial colonization. Only combinations that meet this requirement after 7 days will be further studied (S2 surfaces). S2 surfaces can be tested for colonization and bacterial adhesive strength under flow. S2 surfaces can be pre-incubated with bacteria ($10^2$ cfu/ml), 24 h (±plasma pre-incubation), 37° C. In the first set of experiments, samples can be exposed to static conditions and parallel plate apparatus shear flow at 1-10 dyne/cm$^2$, levels consistent with venous blood flow.

Individual S2 surfaces can be assessed for biofilm and bacterial adhesive strength over time. The most successful surfaces can show significantly decreased bacterial adhesion, even under static conditions.

Methods:

Controls include unmodified chitosan and S1 surfaces without TB.

Visualization of Adherent Viable and Non-Viable Bacteria.

One can distinguish viable from non-viable bacteria with the Live/Dead BACLIGHT system (Molecular Probes), in which live and dead bacteria can be stained with SYTO9+ propidium iodide.

Short-Term Bactericidal Activity.

*S. aureus*, and *P. aeruginosa* will be diluted to 1×$10^2$ cfu/ml and 1 ml of bacteria incubated with surfaces for 6-48 h. Bactericidal activity can be determined after pre-coating the surfaces in PBS. For flow, bacteria will be pre-incubated with surfaces for 24 h, and shear stresses up to 10 dyne/cm$^2$.

Long-Term Bactericidal Activity.

(1) Surfaces can be exposed to ~$10^2$ cfu/ml of bacteria for 4 h, washed, and incubation continued for 24 h in 1% glucose/PBS, 37° C. Surfaces can be (a) harvested for counts or visualization or (b) re-challenged as above for an additional 24 h, for times out to 7 days. (2) Surfaces will be incubated in PBS 1-14 days. Every 3 d surfaces can be challenged with 1×$10^2$ cfu/ml bacteria in PBS, 1% glucose at 37° C. for 24 h, washed three times with PBS to remove loosely adherent bacteria, and bacterial adhesion and viability assessed.

Example 3

Controlled and Localized Release of Tobramycin from a Stimuli-Responsive Grafted Bilayer Challenged with *S. aureus*

In the present study, a novel bilayer brush is introduced having a grafted anionic polymer that serves as a depot for antibiotics and an outer cationic polymer that exhibits orthogonal swelling behavior.

Figure 14:
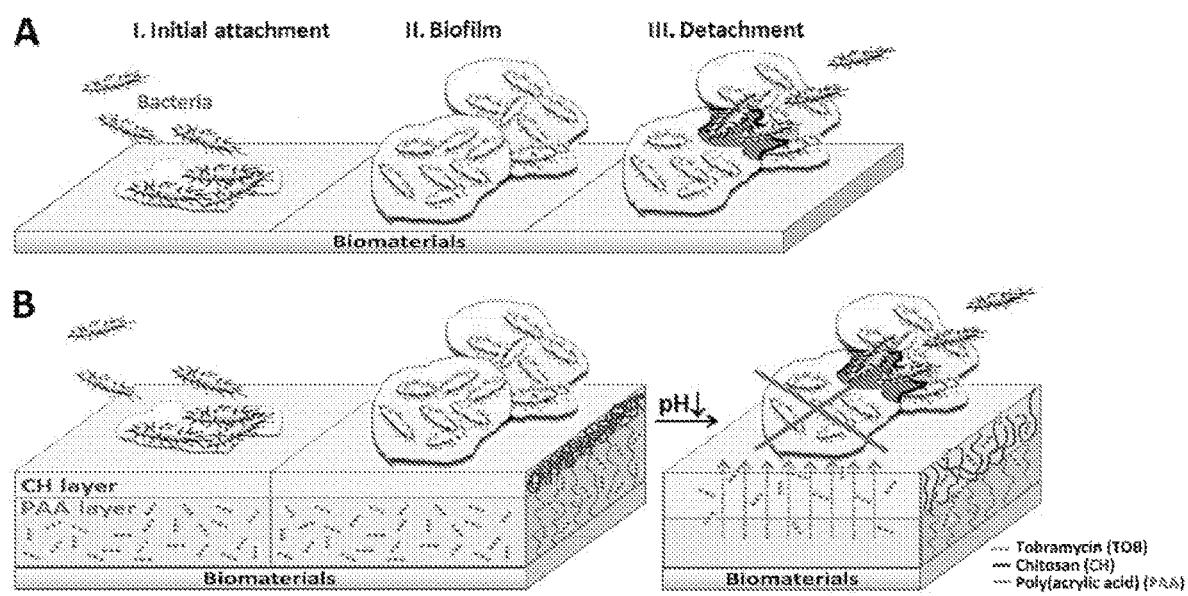
FIG. 14. (A) Bacterial infection on biomaterials involves (I) bacterial attachment, (II) bacterial colonization and biofilm formation, and (III) biofilm detachment for bacterial proliferation. (B) pH-responsive, drug release polymer bilayer system has an outer layer of chitosan (CH, solid lines), which provides biocompatibility and hemocompatibity. This layer minimizes blood coagulation and inflammation when a biomaterial comes in direct contact with biological tissue and provides initial resistance against bacterial infection. An inner layer of poly (acrylic acid) (PAA, dashed lines) is grown from the biomaterial using surface initiated atomic transfer radical polymerization (SI-ATRP). The molecular weight can be varied to tune the loading amount of tobramycin (TOB, open circles) which is electrostatically attracted to the PAA at pH 7. The depicted drug release mechanism is that bacterial colonization and formation of a biofilm on the TOB loaded CH/PAA bilayer causes a local decrease in pH near the infected area (FIG. 14B. II). The reduced local pH triggers the outer CH layer to swell and reduces the electrostatic attraction between PAA and TOB (FIG. 14B. III). TOB loaded in PAA releases and diffuses into biofilm to kill the bacteria (FIG. 14B. IV). In summary, TOB is loaded at pH 4.5, retained at pH 7 and released at low pH.

We grafted a polymer bilayer, comprised of an inner PAA monolayer cross-linked with an outer chitosan (CH) or quaternary modified chitosan (CH-Q) brush to planar and tubular oxide and polymer surfaces, respectively, and characterize bilayer swelling and collapse, the loading and release of antibiotics, and antibacterial and biocompatibility properties. FIG. 14B shows the bilayer construction with the end-grafted PAA brush (dashed lines) cross-linked to the outer CH (solid lines), respectively. Chitosan is a natural polymer that inhibits blood coagulation and inflammatory response upon blood contact (i.e., biocompatible) and resists the attachment of bacteria. Chitosan is insoluble at pH 7 and therefore forms a glassy layer under physiological conditions. Because PAA is anionic, the inner layer is loaded with cationic antibiotics via electrostatic attraction and forms crosslinks with the outer CH layer resulting in a stable bilayer. Tobramycin (TOB), a multi-cationic aminoglycoside antibiotic is chosen as a model drug for loading in PAA. Our proposed drug release mechanism is that bacterial colonization and biofilm formation initiates localized acidification on the bilayer surface. As pH decreases, the initially glassy CH layer hydrates, swells and allows TOB stored in the PAA layer to diffuse into the biofilm and kill bacteria as represented in FIG. 14B (far right). Because bacteria adhesion may depend on modulus, the viscous CH layer can further reject the attached biofilm. Here, pH-responsive swelling, TOB uptake, storage, and release, and bactericidal efficacy of the CH/PAA bilayer are demonstrated.

The CH/PAA bilayer is prepared by first growing a polymer brush from the substrate. As shown in FIG. 5, PAA brushes are end-grafted to silicon oxide using SI-ATRP by polymerizing hydrophobic tert-butyl acrylate (tBA) which is then hydrolyzed using trifluoroacetic acid (TFA) to produce the anionic PAA brush. Attenuated Total Reflectance-FTIR (ATR-FTIR) was used to characterize the surface-grafted polymers before and after the hydrolysis of PtBA. ATR-FTIR results are consistent with complete conversion of PtBA to PAA$^I$ in good agreed with the literature. Quartz Crystal Microbalance with Dissipation (QCM-D) was used to estimate the grafting density of PtBA and PAA$^I$ brushes as well as the percent hydrolysis of PtBA. QCM-D results showed that the dry areal masses of PtBA and PAA' brushes were 31.1±1.1 μg/cm$^2$ and 17.6±0.5 μg/cm$^2$, respectively, which corresponds to 98.8% hydrolysis of tBA. The grafting densities of PtBA and PAA$^I$ were identical, namely 0.78±0.03 chains/nm$^2$ and 0.79±0.02 chains/nm$^2$, respectively, confirming that hydrolysis does not detach grafted chains. In addition, spectroscopic ellipsometry (SE) and contact angle measurements of PtBA and PAA$^I$ brushes yielded the expected values of thickness, reflective index, and contact angle. Namely, the PAA$^I$ brush has a lower dry thickness and water-contact angle than the PtBA brush. The swelling of the PAA$^I$ brush as a function of pH was investigated using in-situ SE. The thickness was 388 um at pH 3.8, 369 nm at pH 5.7, 396 nm at pH 7.2, and 475 nm at pH 10.2. The estimated percent swelling and water content of the PAA$^I$ brush increased as pH increased. Over a pH range of 3.8 to 10.2, the PAA$^I$ brush was thicker and underwent greater swelling relative to cationic brushes of CH and CH-Q. The pH-dependent swelling behavior of the PAA' brush is orthogonal to the CH and CH-Q layers.

To create the CH/PAA$^I$ bilayer, CH is cross-linked to the previously grafted PAA brush. FIG. 5 (bottom) shows that the PAA$^I$ brushes are first activated by sulfo-NHS ester-functionalization, exposed to CH, and then quenched with a NaOH solution (pH~8) to stop the cross-linking. FIG. 5 shows the molecular structure of PAA after esterification (I) and the cross-link between PAA (dashed lines) and CH (solid lines). The dry thickness and reflective index values of the CH and PAA$^I$ layers were 13 nm, 1.478 and 52 nm, 1.533, respectively. FIG. 7 shows the in-situ thickness and water content as a function of pH measured by in-situ SE. First, upon increasing pH from 5.8 to 7.1, the CH thickness and water content decreases strongly from 158 nm to 37 nm, and 97% to 48%, as shown in FIGS. 7a and 7b, respectively. Upon further increasing the pH to 10.2, the CH layer remains collapsed and the water content slightly decreases. Similarly, upon lowing the pH from 5.8 to 2.5 the thickness slightly increases. whereas the water content remains similar in CH. Thus, the dominant pH response for the outer CH layer is between pH 5.8 to 7.1. In contrast to CH, the thickness and water content inner of the PAA$^I$ layer increases from 113 nm to 290 nm and 45% to 83%, respectively, upon increasing pH from 5.8 to 7. Similar to CH, the thickness and swelling of PAA$^I$ shows the greatest response to pH in this region. For both layers, swelling and contraction were completely reversible upon cycling the pH between 2.6 and 10.2

The pH response of CH and PAA$^I$ in the bilayer can be understood by protonation and deprotonation of NH$_2$ and COOH, respectively. For CH, as pH decreases, the amines become protonated (NH$_3^+$) resulting in electrostatic repulsion and swelling. This pH-dependent swelling of the CH in CH/PAA$^I$ is similar to that previously observed for a CH monolayer grafted directly to silicon oxide. For the PAA layer in CH/PAA$^I$, a pH decreases (i.e., approaches the pKa of NH$_2$, 4.6) the equilibrium between COO— and COOH moves towards COOH, namely COO— protonation, and therefore the PAA$^I$ chains have a lower charge and excluded volume is reduced. This behavior for the PAA$^I$ in the bilayer is similar to that observed for a PAA monolayer. Thus, the CH and PAA$^I$ layers in the bilayer exhibit complementary pH-dependent swelling.

To evaluate antimicrobial uptake and release (FIG. 14b), in-situ QCM-D was used to measure TOB loading at low pH, storage at pH 7, and release upon returning to low pH in a PAA$^I$ monolayer and CH/PAA$^I$ bilayer as shown in FIG. 8. After establishing a baseline of 0 at pH 3.8, TOB was introduced into the QCM flow cell at nearly the same pH, 4.0 (arrow 1 in FIG. 8a). Correspondingly, the frequency, $\Delta f_3/3$, and dissipation, $\Delta D_3$, of the PAA$^I$ brush decrease (FIG. 8b), indicating an increase in mass and rigidity, respectively. The mass increase is due to the uptake of TOB and reaches saturation after 15 min. The increase in the PAA$^I$ brush stiffness is consistent with the multi-cationic TOB forming crosslinks between the carboxylate anions on PAA$^I$. The dynamics of cross-linking is extremely fast, occurring within several minutes. This electrostatic crosslinking is similar to the behavior of a cationic CH brush exposed to a multi-anion small molecule, such as citrate. As the pH increases from 4.01 to 7.0 (arrow 2), $\Delta f_3/3$ decreases slightly, whereas $\Delta D_3$ remains nearly constant. This behavior shows that the TOB initially loaded into PAA$^I$ is retained near physiological pH 7.0. Upon decreasing pH from 7.0 to 3.8 (arrow 3), $\Delta f_3/3$ increases rapidly during the initial 20 min., and then more slowly for times up to 40 min (arrow III). This release profiles shows that TOB can diffusion out of PAA$^I$ at low pH.

The QCM-D result for the CH/PAA$^I$ bilayer is shown in FIG. 8b. On exposing the bilayer to TOB (arrow 1 FIG. 8b), the frequency, $\Delta f_3/3$, decreases whereas the dissipation value, $\Delta D_3$, slightly increases, indicating an increase in mass and only a slight increase in viscoelasticity, respectively. The mass increase is attributed to the uptake of TOB due to electrostatic cross-linking between PAA$^I$ and TOB. The small increase in viscosity indicates that the outer CH layer is slightly more swollen and does not adsorb TOB. When pH increases from 4.0 to 7.0 (arrow 2 in FIG. 8b), $\Delta f_3/3$ increases and $\Delta D_3$ decreases. This behavior is attributed to collapse of CH layer at pH 7, similar to that observed for a CH monolayer. This collapse is due to the insolubility of CH at high pH (above ~6.5) which results in the expulsion of water and the formation of a rigid outer layer. Upon decreasing pH from 7.0 to 3.8 (arrow 3), $\Delta D_3$ increases, indicating that CH re-swells upon returning to pH 3.8. In addition, $\Delta f_3/3$ decreases rapidly suggesting a "net" increase in mass due to the swelling of CH. Because TOB release may occur simultaneously with CH swelling, a method to decouple these confounding contributions has been developed as described in the next section.

To quantify uptake and release of TOB by the PAA$^I$ monolayer and CH/PAA bilayer, the frequency and dissipation were measured after drying samples at time points denoted I, II, and II in FIG. 8. In addition to PAA$^I$, a thinner monolayer denoted PAA$^{II}$ was prepared to investigate the effect of PAA thickness on TOB uptake and release. The mass and carboxylic acid areal densities for PAA$^I$ and PAA$^{II}$ are 17.6±0.5 μg/cm$^2$ and 1475±44 [COOH]/nm$^2$, and 8.3±0.2 μg/cm$^2$ and 695±21 [COOH]/nm$^2$, respectively. For PAA$^I$ and CH/PAA$^I$ brushes, the mass and areal TOB density after the TOB uptake are 17,231±236 ng/cm$^2$ (222 molecules/nm$^2$), and 1865±38 ng/cm$^2$ (24 molecules/nm$^2$), respectively. Relative to the carboxylic acid areal density of PAA$^I$ (1475), a TOB loading of 222 molecules/nm$^2$ is plausible. Namely, if five carboxylic acid groups coordinated with one TOB, which has five amino groups, the maximum loading of TOB into PAA$^I$ would be 295 molecules/nm$^2$. Using the same approach, the loading of TOB in CH/PAA$^I$ is 24 molecules/nm$^2$, which is more than ten times less than in the PAA$^I$ monolayer. This result suggests that carboxylic acid groups required for coordination with TOB is greatly reduced because of the crosslinking between CH and PAA$^I$ (FIG. 5).

The amount of TOB released from PAA$^I$ and CH/PAA$^I$ after 30 min exposure to pH 3.8 (III, FIG. 8) is determined. The areal mass and density of residual TOB are 11,560±122 ng/cm$^2$ (149 molecules/nm$^2$) and 1195±60 ng/cm$^2$ (15 molecules/nm$^2$), respectively. Thus, the TOB concentration after 30 min decreases by 33% and 36% in PAA$^I$ and CH/PAA', respectively. By comparison, the areal masses and densities at pH 7.0 (point II in FIG. 8) after TOB uptake by PAA$^{II}$ and CH/PAA$^{II}$ layers are 5,577±150 ng/cm$^2$ (72 molecules/nm$^2$), and 1558±26 ng/cm$^2$ (20±0 molecules/nm$^2$), respectively, as shown in Table 2. Relative to the carboxylic acid groups in PAA$^{II}$ (695±21 [COOH]/nm$^2$), the amount of TOB loaded into PAA$^{II}$ (72 molecules/nm$^2$) is reasonable. As previously mentioned, if five carboxylic acid groups from PAA coordinate with TOB, the maximum loading of TOB into PAA$^{II}$ is 139 molecules/nm$^2$. The residual TOB concentrations in PAA$^{II}$ and CH/PAA$^{II}$ after 30 min (III in FIG. 8) are 4,174±164 ng/cm$^2$ (54±2 molecules/nm$^2$), and 807±31 ng/cm$^2$ (10±2 molecules/nm$^2$), respectively. Compared with PAA$^I$ and CH/PAA$^I$, PAA$^{II}$ and CH/PAA$^{II}$ layers contain less TOB after loading and less TOB after drug release. This difference can be attributed to the lower carboxylic acid density of PAA$^{II}$, suggesting that antibiotic loading can be tuned by controlling the molecular weight of the PAA brush chain via SI-ATRP. In subsequent antibacterial studies, the PAA brush is PAA$^I$ in all cases.

TABLE 2

TOB uptake and release by PAA monolayers and CH/PAA bilayers

| Mono or Bilayer | TOB Stored | | TOB Retained | | % TOB Released |
|---|---|---|---|---|---|
| | Areal mass* (ng/cm$^2$) | Areal density (molecules/nm$^2$) | Areal mass* (ng/cm$^2$) | Areal density (molecules/nm$^2$) | |
| PAA$^I$ | 17231 ± 237 | 222 ± 3 | 11560 ± 122 | 149 ± 2 | 33 ± 0 |
| CH/PAA$^I$ | 1865 ± 38 | 24 ± 0 | 1195 ± 60 | 15 ± 1 | 36 ± 4 |
| PAA$^{II}$ | 5577 ± 150 | 72 ± 2 | 4174 ± 164 | 54 ± 2 | 25 ± 1 |
| CH/PAA$^{II}$ | 1558 ± 26 | 20 ± 0 | 807 ± 31 | 10 ± 0 | 48 ± 1 |

*Areal mass measured by QCM-D based on dried layers. Mean values and standard deviations calculated from three modes, $\Delta f_n/n$ (n = 3, 5, 7); PAA$^I$ brush: areal mass = 17.6 ± 0.5 μg/cm$^2$, dry thickness = 145 ± 4 nm, [COOH]/nm$^2$ = 1475 ± 44; PAA$^{II}$ brush: areal mass = 8.3 ± 0.2 μg/cm$^2$, dry thickness = 68 ± 2 nm, [COOH]/nm$^2$ = 695 ± 21. Methods are described in Supporting Information.

To test antibacterial properties, PAA and CH/PAA were grafted to polyurethane (PU) tubes and exposed to S. aureus for 12 h. Disk diffusion bioassays were performed to demonstrate that TOB did not release at physiological pH. PU, PAA grafted PU (PAA/PU), CH grafted PAA/PU (CH/PAA/PU), TOB loaded PAA/PU (PAA$_{TOB}$/PU), and TOB loaded CH/PAA/PU (CH/PAA$_{TOB}$/PU) were prepared using our recently published methods. TOB loading and storage was identical to the in-situ QCM-D studies, corresponding to arrow II in FIG. 8. Tubes were filled with sterilized PBS (pH 7) at 37° C. for 1 hr and Kirby Bauer discs impregnated with undiluted samples were monitored using S. aureus (ATCC 25923) inoculated agar plates for the presence of a zone of inhibition (ZOI). The absence of a ZOI for each sample indicated that the TOB concentration remained below the lower detection limit of S. aureus. This result indicates that, at most, only negligible amounts of TOB diffused out of the PAA into the PBS, consistent with QCM-D results showing that TOB loaded PAA layers did not release the drug.

Figure 15:
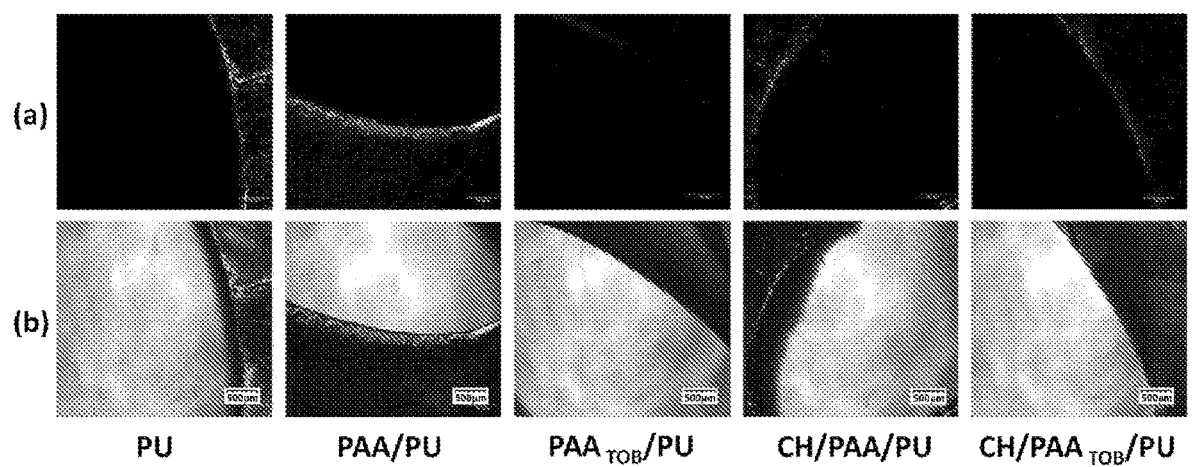
FIG. 15. Representative confocal fluorescence images (a), and confocal images merged with bright field images (b) of fluorescent bacteria (S. aureus AH1710) on PU, PAA/PU, PAA$_{TOB}$/PU, CH/PAA/PU and CH/PAA$_{TOB}$/PU tubes (left to right) after overnight culturing. Each tube was cut open for viewing.

PU, PAA/PU, CH/PAA/PU, PAA$_{TOB}$/PU, and CH/PAA$_{TOB}$/PU tubes were filled with fluorescent bacteria solution (S. aureus AH1710, ~10$^5$ colony forming units/mL (CFU/mL)) and incubated at 37° C. overnight. FIG. 15 shows representative confocal fluorescence images (top row) and fluorescence images merged with bright field images (bottom row) of fluorescent bacteria on the surfaces. Bacteria were observed only on the surfaces of PU, PAA, CH/PAA tubes, indicating bacterial adherence and growth on these materials. In contrast, no fluorescence signal is observed from the PAA$_{TOB}$/PU tube, indicating that PAA$_{TOB}$/PU killed all bacteria. For the CH/PAA$_{TOB}$/PU tube, only weak fluorescence is observed suggesting that even though bilayer loading is almost 10× less than the PAA$_{TOB}$ monolayer bacteria attachment and growth is greatly limited.

Figure 16:
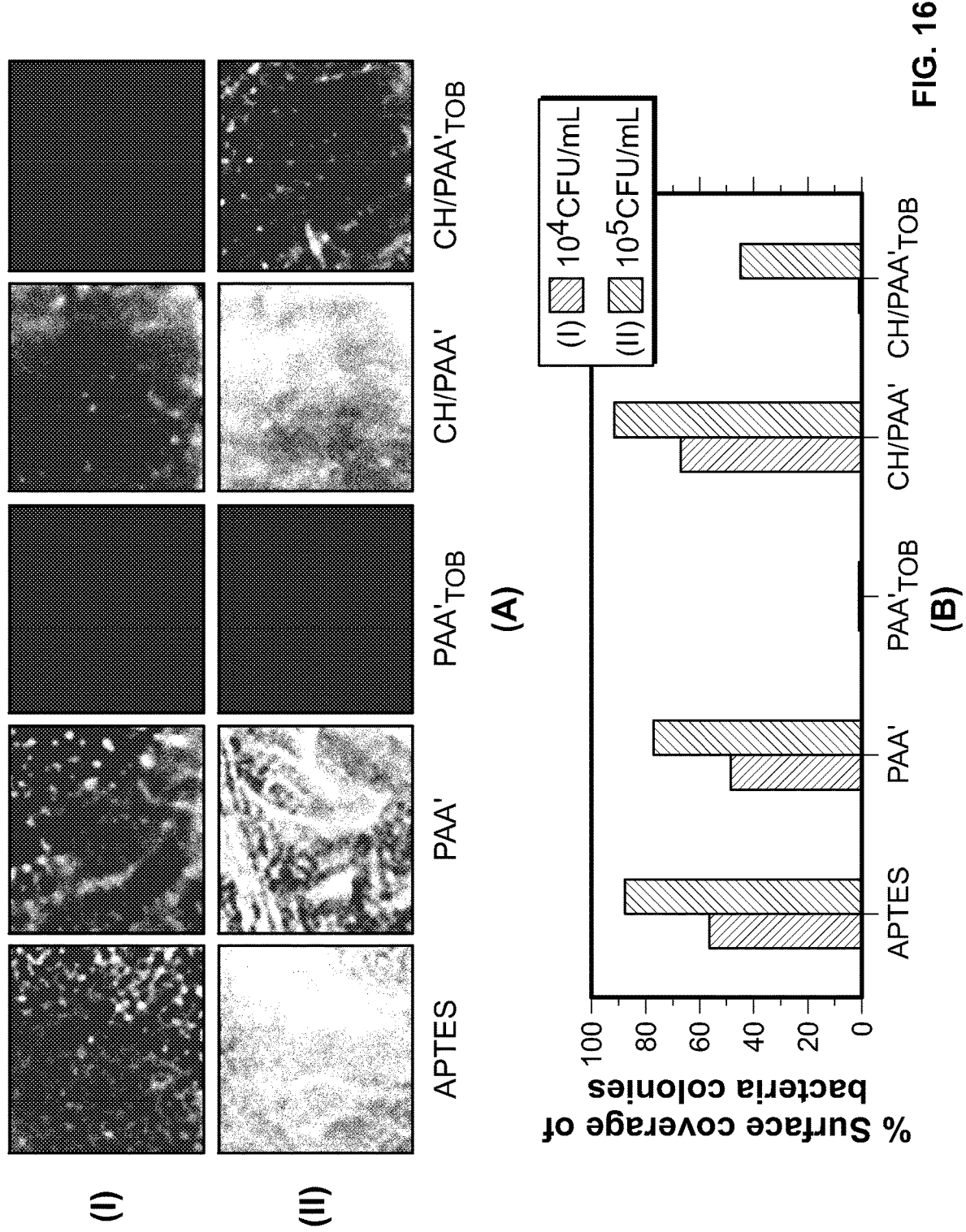
FIG. 16. Optical micrograph images of bacterial colonies on APTES, PAA$^I$, PAA$^I_{TOB}$ (222 TOB molecules/nm$^2$), CH/PAA$^I$, and CH/PAA$^I_{TOB}$ (24 TOB molecules/nm$^2$) after exposure to ~10$^4$ (top row, I) and 10$^5$ (bottom row, II) CFU/mL bacterial solutions (S. aureus ATCC 25923). The size is 7.255×6.765 mm$^2$. B) The bar graph shows the surface coverage of bacteria colonies from optical images analyzed using imageJ. Both PAA$^I_{TOB}$ and CH/PAA$^I_{TOB}$ prevent bacteria attachment and growth at ~10$^4$ CFU/mL. At 10$^5$ CFU/mL, PAA$^I_{TOB}$ prevents bacteria attachment/growth whereas CH/PAA$^I_{TOB}$ shows a lower coverage than all other surfaces.

We further evaluated the dependence of antibacterial efficiency on TOB loading using surfaces previously characterized by QCM-D. Amino-propyl-triethoxy-silane or APTES (as a control), PAA$^I$, PAA$^I_{TOB}$, CH/PAA$^I$ and CH/PAA$^I_{TOB}$ surfaces were exposed to bacterial solutions of S. aureus (ATCC 25923) for 2 hr at 37° C. FIG. 16 shows optical microscopy images for surfaces exposed to ~10$^4$ (I) and ~10$^5$ CFU/mL (II). Although slightly less at ~10$^4$ CFU/mL, bacteria attach to all surfaces without TOB, namely APTES, PAA$^I$, and CH/PAA$^I$. No bacteria attach to the PAA$^I_{TOB}$ at either ~10$^4$ or ~10$^5$ CFU/mL, whereas bacteria attachment is only prevented on CH/PAA$^I_{TOB}$ at ~10$^4$ CFU/mL. To quantify the surface coverage of bacterial colonies, colonies were further grown under a thin film of TSB agar overnight in and incubator and then their areal percentage determined using NIH imageJ software. As shown by the bar graph in FIG. 16, after exposure to ~10$^4$ CFU/mL (bars hatched diagonally from upper left to lower right), the surface coverages are 57%, 48% and 67% on APTES, PAA$^I$ and CH/PAA$^I$, respectively. At ~10$^5$ CFU/mL, the surface coverages are 88%, 77% and 92% on APTES, PAA$^I$ and CH/PAA$^I$, respectively. Although CH is antibacterial, CH/PAA$^I$ exhibits a surface coverage of bacteria that is greater than APTES and PAA$^I$ at both low and high concentrations. S. aureus colonies did not grow on PAA$^I_{TOB}$ at either concentration of bacterial solution. This result indicates that TOB release from PAA$^I_{TOB}$ was sufficient to kill adherent bacteria. For CH/PAA$^I_{TOB}$, S. aureus colonies did not grow at 10$^4$ CFU/mL bacterial solution, but 46% of the surface is covered at 10$^5$ CFU/mL. Thus, TOB release from CH/PAA$^I_{TOB}$ was sufficient to kill adherent bacteria only at the lower bacterial concentration. However, the TOB released from CH/PAA$^I_{TOB}$ was below the killing threshold for adherent bacteria at the higher concentration of bacteria. Nonetheless, these results demonstrate that antibiotic release from thin monolayer and bilayer grafted layers is sufficient to kill adherent bacteria. By increasing the loading of TOB, the efficacy of the bilayer system will be improved in future studies.

A simple, efficient approach to generate multifunctional grafted polymer bilayers on biomaterials was developed by chemically combining a biopolymer as an outer layer and a synthetic polymer as an inner layer. pH-responsive, biocompatible properties were imparted to the outer layer, which, in a clinical application is typically in direct contact with biological tissue. pH-responsive, drug-tunable uptake and release properties were designed into the inner layer, which, in a clinical application, is typically in direct contact with the biomaterial. In addition, antibacterial tests were conducted demonstrating that model drug (e.g., TOB) loaded into the bilayer did not release at physiological pH (pH 7), yet with bacterial growth and its accompanying local acidification, the TOB loaded surface grafted constructs could release sufficient drug to eliminate bacteria from the biomaterial surface. The quantitative antibacterial efficiency shown depends on the drug loading, which is a tunable property of the brush layers described. The antibiotic loading capacity can be increased by increasing the thickness of the PAA layer by increasing the brush length and decreasing the cross-linking of CH and PAA at the bilayer interface. The approach to generate multifunctional grafted polymer bilayers on biomaterials is versatile and applicable to stimuli-responsive macroscale drug delivery systems and stimuli-responsive nano-carriers for drug delivery, as well as implantable medical devices having direct contact with living tissue for biomedical applications.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. An article comprising a substrate comprising a surface, wherein the surface of the substrate comprises:
a first polymer layer comprising an anionic polymer,
a second polymer layer exposed to a biological tissue or a biological system comprising a cationic polymer,
wherein said cationic polymer comprises a chitosan modified with 25% to 50% quaternary ammonium salts, a chitosan modified with about 40% carboxylic acid, or a combination thereof,
wherein said first polymer layer is an end-grafted polymer brush immobilized on the surface of said substrate, and
wherein said second polymer layer overlays, directly contacts, and is covalently cross-linked to said first polymer layer,
and an anti-microbial agent sequestered in said first polymer layer,
wherein said agent is sequestered at a physiological pH, and wherein said polymers are configured to release said agent at an acidic pH.

2. The article of claim 1, wherein said physiological pH ranges from about 7.35 to about 7.45.

3. The article of claim 1, wherein acidic pH ranges from about 2.0 to about 6.9.

4. The article of claim 1, wherein said acidic pH is caused by or associated with bacterial infection from a biofilm.

5. The article of claim 1, wherein said second layer resists adhesion of a microbe to its surface.

6. The article of claim 5, wherein said microbe is a bacterium.

7. The article of claim 6, wherein said bacteria is *Staphylococcus aureus* or *Pseudomonas aeruginosa*.

8. The article of claim 1, wherein said agent comprises a cation.

9. The article of claim 1, wherein said anionic polymer is poly(acrylic acid) (PAA), alginic acid (ALG), poly (aspartic acid), poly (glutamic acid) (PGA), hyaluronic acid, or poly (styrenesulfonate).

10. The article of claim 1, wherein said agent comprises an amine group.

11. The article of claim 1, wherein said agent is an antibiotic.

12. The article of claim 11, wherein said agent is an aminoglycoside.

13. The article of claim 1, wherein said substrate is a medical material, device, or implant.

14. The article of claim 13, wherein said substrate is selected from a catheter, bandage, adhesive, gauze strip, gauze pad, medical or surgical drape, syringe holder, suture, IV tubing, IV bag, stent, guide wire, prosthesis, orthopedic pin, dental material, pacemaker, heart valve, artificial heart, knee and hip joint implant, bone cement, vascular graft, urinary catheter, ostomy port, orthopedic fixture, pacemaker lead, defibrillator lead, ear canal shunt, cosmetic implant, ENT (ear, nose, throat) implant, staple, implantable pump, hernia patch, plate, screw, blood bag, external blood pump, fluid administration system, ventilator, endotracheal tube, heart-lung machine, dialysis equipment, artificial skin, ventricular assist device, hearing aid, or dental implant.

15. The article of claim 1, wherein the surface of said substrate is glass, plastic, metal, or polymer.

16. An anti-microbial material comprising a plurality of polymer layers and an anti-microbial agent sequestered therein, said plurality of polymer layers comprise
a first polymer comprising an anionic polymer and
a second polymer layer exposed to a biological tissue or a biological system comprising a cationic polymer overlaying and directly contacting said first polymer layer,
wherein said cationic polymer comprises a chitosan modified with about 25% to about 50% quaternary ammonium salts, a chitosan modified with about 40% carboxylic acid, or a combination thereof,
wherein said first polymer layer is an end-grafted polymer brush immobilized on the surface of a substrate, and
wherein said second polymer layer overlays and is covalently cross-linked to said first polymer layer,
wherein said agent remains sequestered at a physiological pH, and
wherein said polymers are configured to release said agent at an acidic pH.

17. The material of claim 16, wherein said anionic polymer is poly(acrylic acid) (PAA), alginic acid (ALG), poly (aspartic acid), poly (glutamic acid) (PGA), hyaluronic acid, or poly(styrenesulfonate).

18. The material of claim 16, wherein said anti-microbial agent is an antibiotic.

19. The material of claim 18, wherein said antibiotic is an aminoglycoside.

20. A method for providing an anti-microbial coating on a surface of an article, the method comprising:
immobilizing an anionic polymer on the surface of said article by end-grafting said anionic polymer to form a first polymer brush layer;
coating and covalently cross-linking a cationic polymer directly on the first polymer brush layer to form a second polymer layer exposed to a biological tissue or a biological system, wherein said cationic polymer comprises a chitosan modified with 25% to 50% quaternary ammonium salts, a chitosan modified with about 40% carboxylic acid, or a combination thereof; and
sequestering an anti-microbial agent in said anionic polymer, wherein said agent is sequestered at a physiological pH, and wherein said polymers are configured to release said agent at an acidic pH.

21. The method of claim 20, wherein the step of sequestering said anti-microbial agent comprises the steps of loading the first polymer layer with the anti-microbial agent by exposing the first polymer layer to an acidic pH in the presence of the anti-microbial agent; and raising the pH to a physiological pH.

22. The method of claim 20, wherein the sequestering step is performed prior to the coating of the cationic polymer on the first polymer layer.

23. The method of claim 20, further comprising the step of drying the anti-microbial coating on the surface of the article.

24. The method of claim 20, wherein said anionic polymer layer is poly(acrylic acid) (PAA), alginic acid (ALG), poly (aspartic acid), poly (glutamic acid) (PGA), hyaluronic acid, or poly(styrenesulfonate).

25. The method of claim 20, wherein said agent is an antibiotic.

26. The method of claim 25, wherein said antibiotic is an aminoglycoside.

27. The method of claim 20, wherein said article is a medical material, device or implant.

28. The method of claim 20, wherein the surface of the article is glass, plastic, metal, or polymer.

29. A method for inhibiting a microbial infection associated with the use of a medical material, device, or implant, the method comprising: providing a medical material, device, or implant having a surface coated with the anti-microbial material of claim 16; contacting the coated medical material, device, or implant with a potential source of the microbial infection.

30. An article comprising a substrate comprising a surface, wherein the surface of the substrate comprises:
- a first polymer layer comprising an anionic polymer selected from the group consisting of poly(acrylic acid) (PAA), alginic acid (ALG), poly (aspartic acid), poly (glutamic acid) (PGA), hyaluronic acid, or poly(styrenesulfonate),
- a second polymer layer exposed to a biological tissue or a biological system comprising a cationic polymer selected from the group consisting of a chitosan modified with 25% to 50% quaternary ammonium salts and a chitosan modified with about 40% carboxylic acid,
  - wherein said first polymer layer is an end-grafted polymer brush immobilized on the surface of said substrate, and
  - wherein said second polymer layer overlays directly contacts, and is covalently cross-linked to said first polymer layer,
- and an anti-microbial pathogen agent sequestered in said first polymer layer,
  - wherein said agent is sequestered at a physiological pH, and
  - wherein said polymers are configured to release said agent at an acidic pH.

* * * * *